(12) United States Patent
Egan et al.

(10) Patent No.: US 7,432,254 B2
(45) Date of Patent: Oct. 7, 2008

(54) METHOD FOR TREATING GLAUCOMA IC

(75) Inventors: John J. Egan, New York, NY (US); Dilip Wagle, New York, NY (US); Sara Vasan, New York, NY (US); Martin Gall, Morristown, NJ (US); Stanley Bell, Narberth, PA (US); Edmond Joseph LaVoie, Princeton Junction, NJ (US)

(73) Assignee: Synvista Therapeutics, Inc., Montvale, NJ (US)

( * ) Notice: Subject to any disclaimer, the term of this patent is extended or adjusted under 35 U.S.C. 154(b) by 0 days.

(21) Appl. No.: 10/038,112

(22) Filed: Dec. 31, 2001

(65) Prior Publication Data

US 2002/0160993 A1    Oct. 31, 2002

Related U.S. Application Data

(60) Provisional application No. 60/307,418, filed on Jul. 24, 2001, provisional application No. 60/296,257, filed on Jun. 6, 2001, provisional application No. 60/259,426, filed on Dec. 29, 2000.

(51) Int. Cl.
*A61K 31/541* (2006.01)
*A61K 31/5377* (2006.01)
*A61K 31/426* (2006.01)
*A61K 31/53* (2006.01)
*A61K 31/501* (2006.01)
*A61K 31/497* (2006.01)

(52) U.S. Cl. .............. 514/210.2; 514/227.8; 514/235.5; 514/365; 514/242; 514/252.05; 514/255.05; 514/254.04; 514/326; 514/396; 514/341

(58) Field of Classification Search .................. 514/359, 514/365, 210.2, 227.8, 235.5, 242, 252.05, 514/255.05, 254.4, 305, 326, 396, 341
See application file for complete search history.

(56) References Cited

U.S. PATENT DOCUMENTS

| | | | | | |
|---|---|---|---|---|---|
| 4,540,408 | A | * | 9/1985 | Lloyd | 604/294 |
| 5,017,696 | A | * | 5/1991 | Farmar et al. | 536/18.7 |
| 5,140,048 | A | * | 8/1992 | Ulrich et al. | 514/601 |
| 5,153,205 | A | * | 10/1992 | Lotti | 514/317 |
| 5,656,261 | A | | 8/1997 | Cerami et al. | 424/53 |
| 5,853,703 | A | | 12/1998 | Cerami et al. | 424/53 |
| 5,854,000 | A | * | 12/1998 | Bucala et al. | 435/7.1 |
| 5,985,857 | A | * | 11/1999 | Hudson et al. | 514/89 |
| 6,007,865 | A | | 12/1999 | Cerami et al. | 426/656 |
| 6,121,300 | A | | 9/2000 | Wagle et al. | 514/365 |
| 6,319,934 | B1 | | 11/2001 | Wagle et al. | 514/365 |
| 6,440,749 | B1 | | 8/2002 | Cerami et al. | 436/815 |
| 6,596,745 | B2 | * | 7/2003 | Gall | 514/365 |
| RE38,330 | E | * | 11/2003 | Cerami et al. | 424/53 |
| 6,713,498 | B2 | * | 3/2004 | Gall | 514/361 |
| 6,806,268 | B2 | * | 10/2004 | Gall | 514/228.5 |

FOREIGN PATENT DOCUMENTS

EP      0458589 A1 *    11/1991

* cited by examiner

*Primary Examiner*—Brian-Yong S Kwon
(74) *Attorney, Agent, or Firm*—Ivor R. Elrifi; Matthew Pavao; Mintz, Levin, Cohn, Ferris, Glovsky and Popeo, P.C.

(57) ABSTRACT

Provided is a method of treating or ameliorating or preventing glaucoma, decreasing intraocular pressure or improving or amemliorting ocular accommodation in an animal, including a human comprising administering an intraocular pressure decreasing or accommodation improving amount of a compound of the formula I:

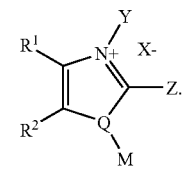

16 Claims, 2 Drawing Sheets

METHOD FOR TREATING GLAUCOMA IC

The present invention claims the priority of U.S. applications No. 60/307,418, filed 24, Jul. 2001, No. 60/296,257, filed 6, Jun. 2001, and No. 60/259,426, filed 29, Dec. 2000.

The present invention relates to methods for treating glaucoma or improving accommodation (i.e. the process by which the eye adjusts for vision at different distances), and to compounds and compositions for use in such treating. In one aspect, the present invention relates to a method of decreasing the intraocular pressure caused by glaucoma.

Diabetes is the major determinant to the development of visual disability and blindness in parts of the world unencumbered by causes related to malnutrition or infectious diseases. Retinopathy is the leading cause of blindness in diabetics and is a progressive, degenerative disease. Of the many risk factors believed to be associated with diabetic retinopathy, the level of glucose in the plasma has been widely investigated. It is well accepted that a lower incidence of retinopathy is associated with decreased plasma levels of glucose.

Ophthalmologic disorders in diabetes include opacification and glaucoma. As the occurrence of these indications is correlated with the persistent hyperglycemia of the disease. Although the incidence of glaucoma is significant in diabetic populations, glaucoma affects a substantial portion of the general aging population as well.

Primary open angle glaucoma occurs in approximately 4% of diabetics compared to 1.8% of the general population. The reasons for the increase in intraocular pressure that is observed in this disorder are not completely understood. The increase in intraocular pressure that characterizes glaucoma is likely caused by an impairment in the drainage of fluid from the eye at the trabecular meshwork since trabeculectomy restores, at least for a period of time, normal intraocular pressures. The origin of this impairment to fluid movement is currently unknown but may be related to a physical obstruction or restriction to movement of proteins that make up a sieving system in the trabecular meshwork. The trabecular meshwork functions as a sieving system that maintains a restricted flow of intraocular fluid from the eye. The result of excess restriction of this flow is a back pressure that causes increased intraocular pressure.

Replacement of the trabecular meshwork (trabeculectomy) remains an established surgical procedure for improving the filtering of intraocular fluid and for overall reduction of intraocular pressure. This remedy is invasive and of limited effectiveness, since pressure elevation frequently recurs after the procedures.

Current chronic pharmaceutical therapies impose a measure of risk on an already medically compromised patient population. The use of topical B-blockers may affect underlying cardiovascular disease, and carbonic anhydrase inhibitors (e.g. Diamox™) may cause metabolic acidosis. The use of pressure-lowering drugs will be affected by the state of renal disease in compromised elderly and diabetic patients. The drawbacks associated with current pharmaceutical therapies highlight an unmet medical need for a chronic pharmaceutical intervention that is distinct in mechanism of action from current therapies.

New strategies for pharmaceutical intervention in the treatment of glaucoma based upon new mechanisms of action need to be identified. In addition, pharmaceutical agents that decrease the intraocular pressure associated with glaucoma are needed. Also, the methods of improving accommodation provided by the invention allow one to avoid costly and burdensome optical solutions, such as the use of separate reading glasses or glasses with bifocal lenses.

SUMMARY OF THE INVENTION

In one embodiment, the invention relates to a method of treating or ameliorating or preventing glaucoma, decreasing intraocular pressure or improving or ameliorating ocular accommodation in an animal, including a human comprising administering an intraocular pressure decreasing or accommodation improving amount of a compound of the formula I:

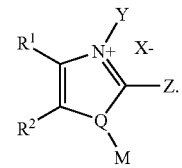

wherein the substituent groups are defined below.

DETAILED DESCRIPTION OF THE INVENTION

Figure 1:
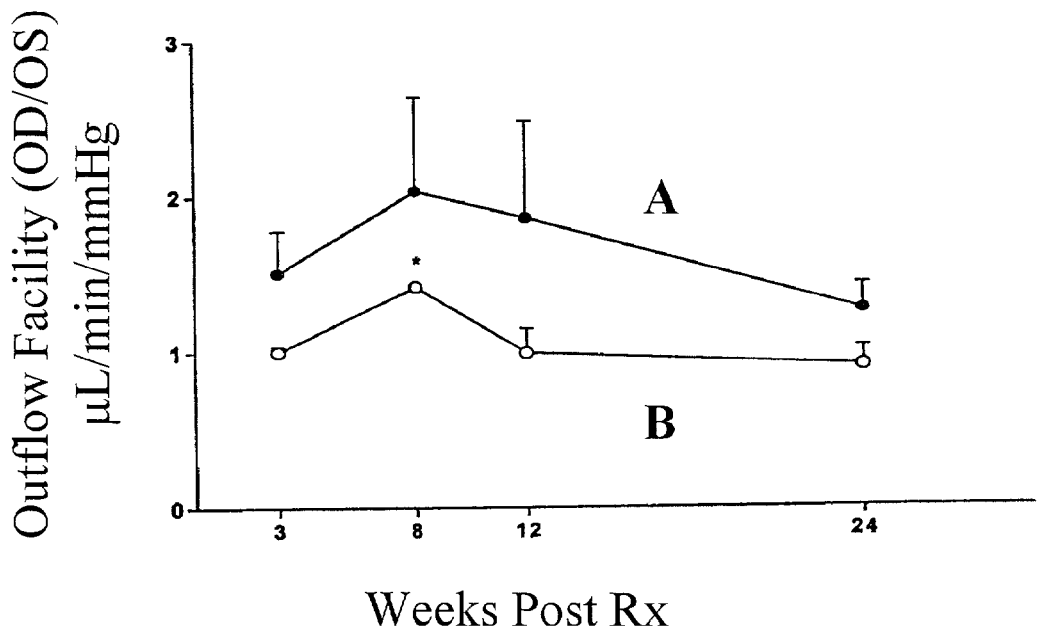
FIG. 1 depicts the effect on outflow facility after intraocular injection of 4,5-dimethyl-3-(2-oxo-2-phenylethyl)-thiazolium chloride.

In accordance with the present invention a method is provided for the treatment of an animal, preferably a mammal, preferably a human with ophthalmologic disorders including glaucoma and reduced accommodation. Briefly the method of the present invention provides for a method of treatment of mammals with glaucoma or reduced accommodation that can be caused by age or certain age-related diseased states such as diabetes. The method provides for administration of classes of inhibitors of advanced glycation. The invention further provides for methods to monitor the improvement in the ocular condition during the course of the administration of compound.

Provided is a method of treating or ameliorating an indication of the invention in an animal, including a human, comprising administering an effective amount of (A) a compound of the formula I:

(I)

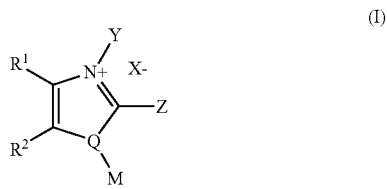

wherein
a. $R^1$ and $R^2$ are
1. independently selected from hydrogen, acylamino, acyloxyalkyl, alkanoyl, alkanoylalkyl, alkenyl, alkoxy, alkoxycarbonyl, alkoxycarbonylalkyl, alkyl, alkylamino, $(C_1-C_3)$alkylenedioxy, allyl, amino, ω-alkylenesulfonic acid, carbamoyl, carboxy, carboxyalkyl, cycloalkyl, dialkylamino, halo, hydroxy, $(C_2-C_6)$hydroxyalkyl, mercapto, nitro, sulfamoyl, sulfonic acid, alkylsulfonyl, alkylsulfinyl, alkylthio, trifluoromethyl, azetidin-1-yl, morpholin-4-yl, thiomorpholin-4-yl, piperidin-1-yl, 4-[$C_6$ or $C_{10}$]arylpiperidin-1-yl, 4-[$C_6$ or $C_{10}$]arylpiperazin-1-yl, Ar {wherein, consistent with the rules of aromaticity, Ar is $C_6$ or $C_{10}$ aryl or a 5- or 6-membered heteroaryl ring, wherein 6-membered heteroaryl ring contains one to three atoms of N, and the 5-membered heteroaryl ring contains from one to three atoms of N or one atom of O or S and zero to two atoms of N, each heteroaryl ring can be fused to a benzene, pyridine, pyrimidine, pyridazine, pyrazine, or (1,2,3)triazine (wherein the ring fusion is at a carbon-carbon double bond of Ar)}, Ar-alkyl, Ar—O, $ArSO_2$—, ArSO—, ArS—, $ArSO_2NH$—, ArNH, (N—Ar)(N-alkyl)N—, ArC(O)—, ArC(O)NH—, ArNH—C(O)—, and (N—Ar)(N-alkyl)N—C(O)—, or together $R_1$ and $R_2$ comprise methylenedioxy [in one embodiment, independently selected from hydrogen, acylamino, acyloxyalkyl, alkanoyl, alkanoylalkyl, alkenyl, alkoxy, alkoxycarbonyl, alkoxycarbonylalkyl, alkyl, $(C_1-C_3)$alkylenedioxy, allyl, ω-alkylenesulfonic acid, carbamoyl, carboxy, carboxyalkyl, cycloalkyl, halo, hydroxy, $(C_2-C_6)$hydroxyalkyl, mercapto, nitro, sulfamoyl, sulfonic acid, alkylsulfonyl, alkylsulfinyl, alkylthio, trifluoromethyl, Ar {wherein, consistent with the rules of aromaticity, Ar is $C_6$ or $C_{10}$ aryl or a 5- or 6-membered heteroaryl ring, wherein 6-membered heteroaryl ring contains one to three atoms of N, and the 5-membered heteroaryl ring contains from one to three atoms of N or one atom of O or S and zero to two atoms of N, each heteroaryl ring can be fused to a benzene, pyrimidine, pyridazine, pyrazine, or (1,2,3)triazine (wherein the ring fusion is at a carbon-carbon double bond of Ar)}, Ar-alkyl, Ar—O, $ArSO_2$—, ArSO—, ArS—, $ArSO_2NH$—, ArNH, (N—Ar)(N-alkyl)N—, ArC(O)—, ArC(O)NH—, ArNH—C(O)—, and (N—Ar)(N-alkyl)N—C(O)—]; or 2. together with their ring carbons form a $C_6$- or $C_{10}$-aromatic fused ring system; or
3. together with their ring carbons form a $C_5-C_7$ fused cycloalkyl ring having up to two double bonds including any fused double bond of the -olium or -onium containing ring, which cycloalkyl ring can be substituted by one or more of the group consisting of alkyl, alkoxycarbonyl, amino, aminocarbonyl, carboxy, fluoro, or oxo substituents [in one embodiment, together with their ring carbons form a $C_5-C_7$ fused cycloalkyl ring having up to two double bonds including the fused double bond of the -olium or -onium containing ring, which cycloalkyl ring can be substituted by one or more of the group consisting of alkyl, alkoxycarbonyl, aminocarbonyl, carboxy, fluoro, or oxo substituents]; or
4. together with their ring carbons form a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring may be optionally substituted with one or more 1-pyrrolidinyl-, 4-[$C_6$ or $C_{10}$]arylpiperazin-1-yl, 4-[$C_6$ or $C_{10}$]arylpiperidin-1-yl, azetidin-1-yl, morpholin-4-yl, thiomorpholin-4-yl, piperidin-1-yl, halo or $(C_1-C_3)$alkylenedioxy groups [in one embodiment, together with their ring carbons form a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring may be optionally substituted with one or more halo or $(C_1-C_3)$alkylenedioxy groups]; or
5. together with their ring carbons form a five to eight membered heterocycle, wherein the heterocycle consists of ring atoms selected from the group consisting of carbon, nitrogen, and $S(O)_n$, where n=0,1, or 2;

b. Z is
1. hydrogen, alkyl Ar—$CH_2$;
2. a group of the formula —$NR^3R^4$, wherein $R^3$ and $R^4$ may be independently hydrogen, alkyl, Ar, or Ar-alkyl-;
3. a group of the formula —$CH(OR^{11})R^{12}$, wherein $R^{11}$ is hydrogen, methyl, ethyl or $CH_3C(O)$—; and $R^{12}$ is [$C_1$ to $C_6$]alkyl, Ar, or $CO_2R^{13}$ wherein $R^{13}$ is hydrogen methyl or ethyl;
4. a group of the formula —$C(CO_2R^{13})(OR^{11})R^{12}$
5. a group of the formula —$CH_2WAr$, wherein W is —(C=O)— or —$S(O)_n$— where n=1 or 2; or
6. a group of the formula —$CH_2C≡C$—$R^{14}$, wherein $R^{14}$ is $(C_1-C_6)$alkyl;

c. Y is
1. amino, or
2. a group of the formula —$CH(R^5)$—$R^6$ wherein
  (a) $R^5$ is hydrogen, alkyl-, cycloalkyl-, alkenyl-, alkynyl-, aminoalkyl-, dialkylaminoalkyl-, (N—[$C_6$ or $C_{10}$]aryl)(N-alkyl)aminoalkyl-, piperidin-1-ylalkyl-, 1-pyrrolidinylalkyl, azetidinylalkyl, 4-alkylpiperazin-1-ylalkyl, 4-alkylpiperidin-1-ylalkyl, 4-[$C_6$ or $C_{10}$]arylpiperazin-1-ylalkyl, 4-[$C_6$ or $C_{10}$]arylpiperidin-1-ylalkyl, azetidin-1-ylalkyl, morpholin-4-ylalkyl, thiomorpholin-4-ylalkyl, piperidin-1-ylalkyl, [$C_6$ or $C_{10}$]aryl, or independently the same as $R^6$ [in one embodiment, hydrogen or alkyl];
  (b) $R^6$ is
    (1) hydrogen, alkyl (which can be substituted by alkoxycarbonyl), alkenyl, alkynyl, cyano- or Rs, wherein Rs is a $C_6$ or $C_{10}$ aryl or a heterocycle containing 4-10 ring atoms of which 1-3 are heteroatoms selected from the group consisting of oxygen, nitrogen and sulfur; or
    (2) a group of the formula —W—$R^7$, wherein $R^7$ is alkyl, alkoxy, hydroxy or Rs, wherein W is —(C=O)— or —$S(O)_n$— where n=1 or 2;
    (3) a group of the formula —W—$OR^8$ wherein $R^8$ is hydrogen or alkyl,
    (4) a group of the formula —CH(OH)Rs; or
    (5) a group of the formula —W—$N(R^9)R^{10}$, wherein
    [a] $R^9$ is hydrogen and $R^{10}$ is an alkyl or cycloalkyl, optionally substituted by
      (i) [$C_6$ or $C_{10}$]aryl, or
      (ii) a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, said heteroaryl ring can be optionally substituted with one or more 1-pyrrolidinyl, 4-[$C_6$ or $C_{10}$]arylpiperazin-1-yl, 4-[$C_6$ or $C_{10}$]arylpiperidin-1-yl, azetidin-1-yl, and morpholin-4-yl, thiomorpholin-4-yl, piperidin-1-yl, halo or $(C_1-C_3)$alkylenedioxy groups, or fused to a substituted phenyl or pyridine ring, wherein the ring fusion is at a carbon-carbon double bond of the heteroaryl ring [in one embodiment, a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, said heteroaryl ring can be optionally substituted with one or more halo or $(C_1-C_3)$alkylenedioxy groups, or fused to a substituted phenyl], or (iii) a heterocycle containing 4-10 ring atoms of which 1-3 are heteroatoms selected from the group consisting of oxygen, nitrogen and sulfur; or

[b] $R^9$ is hydrogen or lower alkyl and $R^{10}$ is Ar; or

[c] $R^9$ is hydrogen or lower alkyl, and $R^{10}$ is a heterocycle containing 4-10 ring atoms of which 1-3 are heteroatoms are selected from the group consisting of oxygen, nitrogen and sulfur, said heterocycle; or

[d] $R^9$ and $R^{10}$ are both alkyl groups; or

[e] $R^9$ and $R^{10}$ together with N form a heterocycle containing 4-10 ring atoms which can incorporate up to one additional heteroatom selected from the group of N, O or S in the ring, wherein the heterocycle is optionally substituted with $(C_6$-or $C_{10})$aryl, $(C_6$-or $C_{10})$arylalkyl, or a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each such heteroaryl can be optionally substituted with one or more 1-pyrrolidinyl, 4-[$C_6$ or $C_{10}$]arylpiperazin-1-yl, 4-[$C_6$ or $C_{10}$]arylpiperidin-1-yl, azetidin-1-yl, morpholin-4-yl, thiomorpholin-4-yl, piperidin-1-yl, halo or $(C_1-C_3)$alkylenedioxy [in one embodiment, $R^9$ and $R^{10}$ together with N form a heterocycle containing 4-10 ring atoms which can incorporate up to one additional heteroatom selected from the group of N, O or S in the ring, wherein the heterocycle is optionally substituted with $(C_6$-or $C_{10})$aryl, $(C_6$- or $C_{10})$arylalkyl, or a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each such heteroaryl can be optionally substituted with one or more halo or $(C_1-C_3)$alkylenedioxy]; or

[f] $R^9$ and $R^{10}$ are both hydrogen;

d. Q is N, O or S;
e. M is absent when Q is O or S;
f. M is alkyl, vinyl or allyl, or independently the same as Y; and
g. X is a pharmaceutically acceptable anion, or (B) a pharmaceutically acceptable salt of the compound, wherein aryl or Ar can be substituted with, in addition to any substitutions specifically noted, one or more substituents selected from the group consisting of acylamino, acyloxyalkyl, alkanoyl, alkanoylalkyl, alkenyl, alkoxy, alkoxycarbonyl, alkoxycarbonylalkyl, alkyl, alkylamino, $(C_1-C_3)$alkylenedioxy, alkylsulfonyl, alkylsulfinyl, ω-alkylenesulfonic acid, alkylthio, allyl, amino, ArC(O)—, ArC(O)NH—, ArO—, Ar—, Ar-alkyl-, carboxy, carboxyalkyl, cycloalkyl, dialkylamino, halo, trifluoromethyl, hydroxy, $(C_2-C_6)$hydroxyalkyl, mercapto, nitro, sulfamoyl, sulfonic acid, 1-pyrrolidinyl, 4-[$C_6$ or $C_{10}$]arylpiperazin-1-yl, 4-[$C_6$ or $C_{10}$]arylpiperidin-1-yl, azetidin-1-yl, morpholin-4-yl, thiomorpholin-4-yl, piperidin-1-yl [in one embodiment, aryl or Ar can be substituted with, in addition to any substitutions specifically noted, one or more substituents selected from the group consisting of acylamino, acyloxyalkyl, alkanoyl, alkanoylalkyl, alkenyl, alkoxy, alkoxycarbonyl, alkoxycarbonylalkyl, alkyl, $(C_1-C_3)$alkylenedioxy, alkylsulfonyl, alkylsulfinyl, ω-alkylenesulfonic acid, alkylthio, allyl, ArC(O)—, ArC(O)NH—, ArO—, Ar—, Ar-alkyl-, carboxy, carboxyalkyl, cycloalkyl, halo, trifluoromethyl, hydroxy, $(C_2-C_6)$hydroxyalkyl, mercapto, nitro, sulfamoyl, sulfonic acid]; and p1 wherein heterocycles, except those of Ar, can be substituted with, in addition to any substitutions specifically noted, acylamino, alkanoyl, alkoxy, alkoxycarbonyl, alkoxycarbonylalkyl, alkyl, alkylamino, alkylsulfonyl, alkylsulfinyl, alkylthio, amino, ArC(O)—, ArO—, Ar—, carboxy, dialkylamino, fluoro, fluoroalkyl, difluoroalkyl, hydroxy, mercapto, sulfamoyl, or trifluoromethyl [in one embodiment, heterocycles, except those of Ar, can be substituted with, in addition to any substitutions specifically noted, acylamino, alkanoyl, alkoxy, alkoxycarbonyl, alkoxycarbonylalkyl, alkyl, alkylsulfonyl, alkylsulfinyl, alkylthio, ArC(O)—, ArO—, Ar—, carboxy, fluoro, fluoroalkyl, difluoroalkyl, hydroxy, mercapto, sulfamoyl, or trifluoromethyl].

In one embodiment, the compound of formula I, is that wherein Y is according to formula —CH($R^5$)$R^6$. In another embodiment, the compound of formula I, is that of formula I, wherein Y is according to formula —CH($R^5$)—W—$R^7$. In another embodiment, the compound of formula I, is that of formula I, wherein Y is according to formula —CH($R^5$)—W—Rs. In another embodiment, the compound of formula I, is that of formula I, wherein $R^1$ and $R^2$ together with their ring carbons form a $C_6$- or $C_{10}$-aromatic fused ring which can be substituted by one or more halo, amino, alkyl, sulfonic acid, alkylsulfonyl or ω-alkylenesulfonic acid groups, or a $C_1-C_3$ alkylenedioxy group with the proviso that when Q is nitrogen $R^1$ and $R^2$ do not form a $C_6$ fused aromatic ring. In another embodiment, the compound of formula I, is that of the compound of formula I, wherein Q is S, and Y and Z are both —NH$_2$.

Further provided are compounds of formula II:

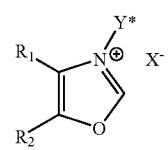

(II)

wherein
a. $R^1$ and $R^2$ are as set forth above;
b. Y* is a group of the formula —CH($R^5$)—$R^6$ wherein
(a) $R^5$ is hydrogen, alkyl-, cycloalkyl-, alkenyl-, alkynyl-, aminoalkyl-, dialkylaminoalkyl-, (N—[$C_6$ or $C_{10}$]aryl)(N-alkyl)aminoalkyl-, piperidin-1-ylalkyl-, 1-pyrrolidinylalkyl, azetidinylalkyl, 4-alkylpiperazin-1-ylalkyl, 4-alkylpiperidin-1-ylalkyl, 4-[$C_6$ or $C_{10}$]arylpiperazin-1-ylalkyl, 4-[$C_6$ or $C_{10}$]arylpiperidin-1-ylalkyl, azetidin-1-ylalkyl, morpholin-4-ylalkyl, thiomorpholin-4- ylalkyl, piperidin-1-ylalkyl, [$C_6$ or $C_{10}$]aryl, or independently the same as $R^6$ (in one embodiment, $R^5$ is hydrogen or alkyl);

(b) $R^6$ is
(1) cyano or $R_T$, wherein $R_T$ is a $C_6$ or $C_{10}$ aryl (in one embodiment, cyano);
(2) a group of the formula —W—Rs, wherein W is —C(=O)— or —S(O)$_n$— where n=1 or 2, and Rs is a $C_6$ or $C_{10}$ aryl or a heterocycle containing 4-10 ring atoms of which 1-3 are heteroatoms selected from the group consisting of oxygen, nitrogen and sulfur;
(3) a group of the formula —W—N($R^9$)$R^{10}$, wherein
    [a] $R^9$ is hydrogen and $R^{10}$ is an alkyl or cycloalkyl, optionally substituted by
        (i) [$C_6$ or $C_{10}$]aryl, or
        (ii) a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, said heteroaryl ring can be optionally substituted with one or more 1-pyrrolidinyl, 4-[$C_6$ or $C_{10}$]arylpiperazin-1-yl, 4-[$C_6$ or $C_{10}$]arylpiperidin-1-yl, azetidin-1-yl, and morpholin-4-yl, thiomorpholin-4-yl, piperidin-1-yl, halo or ($C_1$-$C_3$)alkylenedioxy groups, or fused to a phenyl or pyridine ring, wherein the ring fusion is at a carbon-carbon double bond of the heteroaryl ring (in one embodiment, the optional substituents are one or more halo or ($C_1$-$C_3$)alkylenedioxy groups, or fused to a phenyl, which phenyl can be substituted with the general substitutions), or
        (iii) a heterocycle containing 4-10 ring atoms of which 1-3 are heteroatoms selected from the group consisting of oxygen, nitrogen and sulfur; or
    [b] $R^9$ is hydrogen or lower alkyl and $R^{10}$ is Ar; or
    [c] $R^9$ is hydrogen or lower alkyl, and $R^{10}$ is a heterocycle containing 4-10 ring atoms of which 1-3 are heteroatoms are selected from the group consisting of oxygen, nitrogen and sulfur, or
    [d] $R^9$ and $R^{10}$ are both alkyl groups; or
    [e] $R^9$ and $R^{10}$ together with N form a heterocycle containing 4-10 ring atoms which can incorporate up to one additional heteroatom selected from the group of N, O or S in the ring, wherein the heterocycle is optionally substituted with ($C_6$-or $C_{10}$)aryl, ($C_6$-or $C_{10}$)arylalkyl, or a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each such heteroaryl can be optionally substituted with one or more 1-pyrrolidinyl, 4-[$C_6$ or $C_{10}$]arylpiperazin-1-yl, 4-[$C_6$ or $C_{10}$]arylpiperidin-1-yl, azetidin-1-yl, morpholin-4-yl, thiomorpholin-4-yl, piperidin-1-yl, halo or ($C_1$-$C_3$) alkylenedioxy (in one embodiment, the optional substituents are one or more halo or ($C_1$-$C_3$)alkylenedioxy); or
    [f] $R^9$ and $R^{10}$ are both hydrogen; and
g. X is a pharmaceutically acceptable anion, or (B) a pharmaceutically acceptable salt of the compound, wherein aryl or Ar can be substituted with, in addition to any substitutions specifically noted, one or more of the Aryl General Substitutions or the Aryl Preferred General Substitutions;

wherein heterocycles, except those of Ar, can be substituted with, in addition to any substitutions specifically noted, the Heterocycle General Substitutions or the Heterocycle Preferred General Substitutions;

wherein the compound of formula II differs from a salt of 3-[2-(3,5-dimethoxyphenyl)-2-oxoethyl]-oxazolium by one or more of the lack or replacement of one of the methoxy substitutions, or the presence of one or more additional substitutions [preferably the differences in substitutions total two or more]; and wherein the compound of formula II differs from a salt of 5-phenyl-3-phenylmethyl-oxazolium by one or more of the lack or replacement of the 5-phenyl substitution, or the presence of one or more additional substitutions [preferably the differences in substitutions total two or more).

Also provided are pharmaceutical formulations of compounds of formula II and a pharmaceutically acceptable excipient. The compounds of formula II are useful in the methods of the invention.

5-Phenyl-3-phenylmethyl-oxazolium chloride is described in Takamizawa et al., *Chem. Pharm. Bull.* 22(7): 1526-41, 1974, as an intermediate for synthesizing 1,4-oxazin-3-one and azetidin-2-one derivatives. 3-[2-(3,5-Dimethoxyphenyl)-2-oxoethyl]-oxazolium is described in *J. Med. Chem.* 32: 2301-6, 1989, as an inactive member of a series of compounds that sought to explore the glucose lowering effect of, particularly, certain imidazolium compounds.

In addition to the methods, compounds, and compositions thereof described herein, the invention provides methods or use in the treatments of the invention, or in the manufacture of a medicament for such therapeutic use.

Primary open angle glaucoma is characterized by an increase in intraocular pressure. The condition of open angle glaucoma is characterized by an increase in the pressure within a person's eye or eyes, called the intraocular pressure. The normal pressure is about 15 mmHg. Elevated pressures of 20-30 mm Hg create a strong risk of damage to the optic nerve and blindness.

Glucose reacts with proteins by a non-enzymatic, post-translational modification process called non-enzymatic glycosylation. The resulting sugar-derived adduct, the advanced glycosylation end product (AGE), matures to a molecular species that is reactive, and can readily bond to amino groups on adjacent proteins, resulting in the formation of AGE cross-links between proteins.

It has now been found that certain compounds that inhibit the formation of such sugar-derived adducts, or in some cases are believed to deactivate such adducts or break resulting crosslinks, can reduce intraocular pressure or ameliorate a trend towards elevated pressure.

Structural matrix proteins isolated from tissues of diabetics and aged individuals are more highly crosslinked than those from nondiabetics or younger individuals and are more resistant to both enzymatic and chemical hydrolysis in vitro. It is this cross-linked state of proteins that is believed to cause stiffness of tissues. The cleavage of AGE cross-links between proteins can provide a mechanism-based therapy for restoration of normal tissue function. An agent that cleaves AGE cross-links between proteins or inhibits their formation can restore more normal sieving function and movement to the trabecular meshwork.

In accordance with the present invention, methods for administering pharmaceutical compositions containing certain compounds have been developed for reducing the intraocular pressure associated with glaucoma. These agents are either substituted thiazolium, oxazolium, or imidazolium agents as shown in the Summary section above.

Pharmaceutical compositions of the invention include administering an intraocular pressure decreasing amount of a compound of the formula I.

The alkyl, and alkenyl groups referred to below include both C1 to C6 linear and branched alkyl and alkenyl groups, unless otherwise noted. Alkoxy groups include linear or branched C1 to C6 alkoxy groups, unless otherwise noted.

"Ar" (consistent with the rules governing aromaticity) refers to a $C_6$ or $C_{10}$ aryl, or a 5 or 6 membered heteroaryl ring. The heteroaryl ring contains at least one and up to three atoms of N for the 6 membered heteroaryl ring. The 5 membered heteroaryl ring contains; (1) from one to three atoms of N, or (2) one atom of O or S and zero to two atoms of N. The aryl or heteroaryl is optionally substituted as set forth below. Nonlimiting examples of heteroaryl groups include: pyrrolyl, furanyl, thienyl, pyridyl, oxazolyl, pyrazolyl, pyrimidinyl, and pyridazinyl.

"Ar" can be fused to either a benzene, pyridine, pyrimidine, pyridazine, or (1,2,3) triazine ring.

"Rs" refers to a $C_6$ or $C_{10}$ aryl group (optionally substituted as set forth below) or a heterocycle containing 4-10 ring members and 1-3 heteroatoms selected from the group consisting of oxygen, nitrogen and sulfur (wherein said heterocycle is optionally substituted as set forth below). Where Rs is a non aromatic heterocycle containing sulfur atom as ring members, the sulfur atoms can exist in various oxidation states, as $S(O)_n$, where n is 0,1, or 2.

As used herein, $C_6$ or $C_{10}$ aryl groups and heterocycles containing 4 to 10 ring members are monocyclic or bicyclic. The ring fusions of the bicyclic heterocycles are at carbon-carbon bonds.

In certain embodiments of the invention, the thiazoliums, imidazoliums, and oxazoliums of the invention contain $R^1$ and $R^2$ substitutions that together with their ring carbons (the C4-C5 carbons of the thiazoliums, imidazoliums, and oxazoliums) form a fused C5 to C7 cycloalkyl ring having up to two double bonds including the fused double bond (the C4-C5 double bond of the thiazoliums, imidazoliums, and oxazoliums). The cycloalkyl ring can be substituted by one or more of the group consisting of alkyl, alkoxycarbonyl, amino, aminocarbonyl, carboxy, fluoro, and oxo substituents. One of ordinary skill in the art will recognized that where cycloalkyl groups contain double bonds, the $sp^2$ hybridized carbon atoms can contain only one substituent (which can not be amino- or oxo-). $Sp^3$ hybridized carbon atoms in the cycloalkyl ring can be geminally substituted with the exception that (1) two amino groups and (2) one amino and one fluoro group can not be substituted on the same $sp^3$ hybridized carbon atom.

In certain embodiments of the invention, the thiazoliums, imidazoliums, and oxazoliums of the invention contain $R^1$ and $R^2$ substitutions that together with their ring carbons (the C4-C5 carbons of the thiazoliums, imidazoliums, and oxazoliums) form a five to eight membered heterocycle (i.e. a bicyclic heterocycle is formed). In these embodiments the heterocycle is preferably not aromatic. Particular compounds within these embodiments contain sulfur atoms in the ring fused to the thiazoliums, imidazoliums, and oxazoliums. These sulfur atoms in these particular compounds can exist in various oxidation states, as $S(O)_n$, where n is 0,1, or 2.

In certain embodiments of the invention, the thiazoliums, imidazoliums, and oxazoliums of the invention contain $R^1$ and $R^2$ substitutions that together with their ring carbons (the C4-C5 carbons of the thiazoliums, imidazoliums, and oxazoliums) form a five or six membered heteroaryl ring (i.e. a bicyclic aromatic heterocycle is formed). A preferred bicyclic aromatic heterocycle of the invention is a purine analog [Q is N and $R^1$ and $R^2$ together with their ring carbons (the C4 and C5 of the imidazolium ring) form a pyrimidine ring].

In certain embodiments, the thiazoliums, imidazoliums, and oxazoliums of the invention contain a Y group which can be —$CH(R^5)$—$R^6$. In those embodiments wherein $R^5$ is alkenyl, preferably alkenyl is —C=C—$R^E$, where $R^E$ is alkyl, $H_s$ or hydroxy($C_1$-$C_6$)alkyl. In those embodiments wherein $R^5$ is alkynyl, preferably alkynyl is —C≡C—$R^F$, where $R^F$ is alkyl, hydrogen, or hydroxy($C_1$-$C_6$)alkyl.

Aryl or Ar, can generally be substituted with, in addition to any substitutions specifically noted one or more substituents selected from the group consisting of acylamino, acyloxyalkyl, alkanoyl, alkanoylalkyl, alkenyl, alkoxy, alkoxycarbonyl, alkoxycarbonylalkyl, alkyl, alkylamino, (C1-C3)alkylenedioxy, alkylsulfonyl [alkylS(O)$_2$-], alkylsulfinyl [alkylS(O)—], ω-alkylenesulfonic acid [-alkylSO$_3$H where n=1-6)], alkylthio, allyl, amino, ArC(O)—, ArO—, Ar—, Ar-alkyl-, carboxy, carboxyalkyl, cycloalkyl, dialkylamino, halo, trifluoromethyl, hydroxy, (C2-C6)hydroxyalkyl, mercapto, nitro, sulfamoyl, sulfonic acid [—SO$_3$H], 1-pyrrolidinyl-, 4-[C6 or C10]arylpiperazin-1-yl-, 4-[C6 or C10]arylpiperidin-1-yl, azetidin-1-yl, morpholin-4-yl and piperidin-1-yl.

Heterocycles, except those of Ar, can generally be substituted with acylamino, alkanoyl, alkoxy, alkoxycarbonyl, alkoxycarbonylalkyl, alkyl, alkylamino, alkylsulfonyl [alkylS(O)$_2$—], alkylsulfinyl [alkylS(O)—], alkylthio, amino, ArC(O)—, ArO—, Ar—, carboxy, dialkylamino, fluoro, fluoroalkyl, difluoroalkyl, hydroxy, mercapto, sulfamoyl, or trifluoromethyl. Preferably multiple substituents are located on different atoms of the heterocyclic ring, with the proviso that alkyl, alkylcarbonyl, and fluoro substituents can be substituted on the same carbon atom of the heterocyclic ring. Heterocycles can be substituted with one or more substituents.

The halo atoms can be fluoro, chloro, bromo or iodo. Chloro and fluoro are preferred for aryl substitutions.

For the purposes of this invention, the compounds of formula (I) are formed as biologically or pharmaceutically acceptable salts. Useful salt forms include the halides, (particularly bromides and chlorides) tosylated, methanesulfonated, brosylates, fumarates, maleates, succinates, acetates, mesitylenesulfonates and the like. Other related salts can be formed using similarly non-toxic, and biologically or pharmaceutically acceptable anions. Representative, non-limiting examples of compounds of the present invention are:

3-[2-(3-phenyl-5-isoxazolyl)-2-oxoethyl]thiazolium bromide

3-[2-(3-phenyl-5-isoxazolyl)-2-oxoethyl]-4,5-dimethylthiazolium bromide

3-[2-(3-phenyl-5-isoxazolyl)-2-oxoethyl]-4-methyl-5-(2-hydroxyethyl)thiazolium bromide 3-[2-[4-(2-ethoxy-2-oxoethyl)-2-thiazolyl]amino-2-oxoethyl]-4,5-dimethylthiazolium chloride 3-[2-(3-phenyl-5-isoxazolyl)-2-oxoethyl]-4-methyl-5-(6-hydroxyhexyl)thiazolium bromide 3-[2-(2,6-dimethyl-4-morpholinyl)-2-oxoethyl]-4,5-dimethylthiazolium bromide 3-(2-(1-piperidinyl)-2-oxoethyl)-4,5-dimethylthiazolium bromide 3-(2-(2-furanyl)-2-oxoethyl)-4,5-dimethylthiazolium bromide 3-(2-(2-furanyl)-2-oxoethyl)-4-(2-hydroxypentyl)thiazolium bromide 3-[2-(2-oxo-1,2,3,4-tetrahydro-6-quinolinyl)-2-oxoethyl]-4,5-dimethylthiazolium bromide
3-(2-(1-pyrrolidinyl)-2-oxoethyl)-4,5-dimethylthiazolium bromide
3-[2-(3-methyl-2-thianaphthenyl)-2-oxoethyl]-4,5-dimethylthiazolium bromide
3-[2-(4-phenyl-1-piperazinyl)-2-oxoethyl]-4,5-dimethylthiazolium bromide
3-(2-(2-thienyl)-2-oxoethyl)-4,5-dimethylthiazolium bromide
3-(2-(2-thienyl)-2-oxoethyl)-4-methyl-5-(2-hydroxyethyl)thiazolium bromide
3-(2-(4-thiomorpholinyl)-2-oxoethyl)-4,5-dimethylthiazolium bromide
3-(2-(hexahydro-1-azepinyl)-2-oxoethyl)-4,5-dimethylthiazolium bromide
3-[2-(4-[2-methoxyphenyl]-1-piperazinyl)-2-oxoethyl]-4,5-dimethylthiazolium chloride
3-(2-(octahydro-1-azocinyl)-2-oxoethyl)-4,5-dimethylthiazolium bromide
3-(2-(2-pyridinyl)-2-oxoethyl)-4,5-dimethyl-thiazolium bromide
3-[2-(2-methyl-1-piperidinyl)-2-oxoethyl]-4,5-dimethylthiazolium chloride
3-[2-(2,6-dimethyl-1-piperidinyl)-2-oxoethyl]-4,5-dimethylthiazolium chloride
3-[2-(4-benzyl-1-piperidinyl)-2-oxoethyl]-4,5-dimethylthiazolium chloride
3-[2-(4-benzyl-1-piperazinyl)-2-oxoethyl]-4,5-dimethylthiazolium chloride
3-[2-(3-phenyl-5-isoxazolyl)-2-oxoethyl]-4-octylthiazolium bromide
3-(2-(4-morpholinyl)-2-oxoethyl)-4,5-dimethylthiazolium bromide
3-[2-[4-(2-ethoxy-2-oxoethyl)-2-thiazolyl]amino-2-oxoethyl]-4,5-dimethylthiazolium chloride
3-(2-(4-morpholinyl)-2-oxoethyl)-4,5-dioctadecylthiazolium bromide
3-[2-(2,6-dimethyl-4-morpholinyl)-2-oxoethyl]-4,5-dipentylthiazolium bromide
3-[2-(1-piperidinyl)-2-oxoethyl]-4,5-didodecylthiazolium bromide
3-(2-(2-furanyl)-2-oxoethyl)-5-decylthiazolium bromide
3-[2-(2-oxo-1,2,3,4-tetrahydro-6-quinolinyl)-2-oxoethyl]-4,5-dioctylthiazolium bromide
3-(2-(1-pyrrolidinyl)-2-oxoethyl)-4,5-diethylthiazolium bromide
3-[2-(3-methyl-2-thianaphthenyl)-2-oxoethyl]-4,5-dipentylthiazolium bromide
3-[2-(4-phenyl-1-piperazinyl)-2-oxoethyl]thiazolium bromide
3-(2-(2-thienyl)-2-oxoethyl)thiazolium bromide
3-(2-(2-thienyl)-2-oxoethyl)-4-methyl-5-(6-hydroxyhexyl)thiazolium bromide
3-(2-(4-thiomorpholinyl)-2-oxoethyl)thiazolium bromide
3-(2-(hexahydro-1-azepinyl)-2-oxoethyl)-4,5-dioctylthiazolium bromide
3-(2-(octahydro-1-azocinyl)-2-oxoethyl)-4,5-didecylthiazolium bromide
3-(2-(2-pyridinyl)-2-oxoethyl)-4,5-dioctylthiazolium bromide
3-[2-(2-methyl-1-piperidinyl)-2-oxoethyl]-4,5-dipropylthiazolium chloride
3-[2-(2,6-dimethyl-1-piperidinyl)-2-oxoethyl]-4-methylthiazolium chloride
3-[2-(4-benzyl-1-piperidinyl)-2-oxoethyl]-5-methylthiazolium chloride
3-[2-(4-benzyl-1-piperazinyl)-2-oxoethyl]-4-octylthiazolium chloride
3-aminothiazolium mesitylenesulfonate;
3-amino-4,5-dimethylaminothiazolium mesitylenesulfonate;
2,3-diaminothiazolinium mesitylenesulfonate;
3-(2-methoxy-2-oxoethyl)thiazolium bromide;
3-(2-methoxy-2-oxoethyl)-4,5-dimethylthiazolium bromide;
3-(2-methoxy-2-oxoethyl)-4-methylthiazolium bromide;
3-(2-phenyl-2-oxoethyl)-4-methylthiazolium bromide;
3-(2-phenyl-2-oxoethyl)-4,5-dimethylthiazolium bromide;
3-amino-4-methylthiazolium mesitylenesulfonate;
3-(2-methoxy-2-oxoethyl)-5-methylthiazolium bromide;
3-(3-(2-phenyl-2-oxoethyl)-5-methylthiazolium bromide;
3-[2-(4-bromophenyl)-2-oxoethyl]thiazolium bromide;
3-[2-(4-bromophenyl)-2-oxoethyl]-4-methylthiazolium bromide;
3-[2-(4-bromophenyl)-2-oxoethyl]-5-methylthiazolium bromide;
3-[2-(4-bromophenyl)-2-oxoethyl]-4,5-dimethylthiazolium bromide;
3-(2-methoxy-2-oxoethyl)-4-methyl-5-(2-hydroxyethyl)thiazolium bromide;
3-(2-phenyl-2-oxoethyl)-4-methyl-5-(2-hydroxyethyl)thiazolium bromide;
3-[2-(4-bromophenyl)-2-oxoethyl]-4-methyl-5-(2-hydroxyethyl)thiazolium bromide;
3,4-dimethyl-5-(2-hydroxyethyl)thiazolium iodide;
3-ethyl-5-(2-hydroxyethyl)-4-methylthiazolium bromide;
3-benzyl-5-(2-hydroxyethyl)-4-methylthiazolium chloride;
3-(2-methoxy-2-oxoethyl)benzothiazolium bromide;
3-(2-phenyl-2-oxoethyl)benzothiazolium bromide;
3-[2-(4'-bromophenyl)-2-oxoethyl]benzothiazolium bromide;
3-(carboxymethyl)benzothiazolium bromide;
2,3-(diamino)benzothiazolium mesitylenesulfonate;
3-(2-amino-2-oxoethyl)thiazolium bromide;
3-(2-amino-2-oxoethyl)-4-methylthiazolium bromide;
3-(2-amino-2-oxoethyl)-5-methylthiazolium bromide;
3-(2-amino-2-oxoethyl)-4,5-dimethylthiazolium bromide;
3-(2-amino-2-oxoethyl)benzothiazolium bromide;
3-(2-amino-2-oxoethyl)-4-methyl-5-(2-hydroxyethyl)thiazolium bromide;
3-amino-5-(2-hydroxyethyl)-4-methylthiazolium mesitylenesulfonate;
3-(2-methyl-2-oxoethyl)thiazolium chloride;
3-amino-4-methyl-5-(2-acetoxyethyl)thiazolium mesitylenesulfonate;
3-(2-phenyl-2-oxoethyl)thiazolium bromide;
3-(2-methoxy-2-oxoethyl)-4-methyl-5-(2-acetoxyethyl)thiazolium bromide;
3-(2-amino-2-oxoethyl)-4-methyl-5-(2-acetoxyethyl)thiazolium bromide;
2-amino-3-(2-methoxy-2-oxoethyl)thiazolium bromide;
2-amino-3-(2-methoxy-2-oxoethyl)benzothiazolium bromide;
2-amino-3-(2-amino-2-oxoethyl)thiazolium bromide;
2-amino-3-(2-amino-2-oxoethyl)benzothiazolium bromide;
3-[2-(4-methoxyphenyl)-2-oxoethyl]thiazolium bromide;
3-[2-(2,4-dimethoxyphenyl)-2-oxoethyl]thiazolium bromide;
3-[2-(4-fluorophenyl)-2-oxoethyl]thiazolium bromide;
3-[2-(2,4-difluorophenyl)-2-oxoethyl]thiazolium bromide;
3-[2-(4-diethylaminophenyl)-2-oxoethyl]thiazolium bromide;
3-propargylthiazolium bromide;
3-propargyl-4-methylthiazolium bromide;
3-propargyl-5-methylthiazolium bromide;

3-propargyl-4,5-dimethylthiazolium bromide;
3-propargyl-4-methyl-5-(2-hydroxyethyl)-thiazolium bromide;
3-(2-[3-methoxyphenyl]-2-oxoethyl)thiazolium bromide;
3-(2-[3-methoxyphenyl]-2-oxoethyl)-4-methyl-5-(2-hydroxyethyl)thiazolium bromide;
3-(2-[3-methoxyphenyl)-2-oxoethyl)-benzothiazolium bromide;
2,3-diamino-4-chlorobenzothiazolium mesitylenesulfonate;
2,3-diamino-4-methylthiazolium mesitylenesulfonate;
3-amino-4-methyl-5-vinylthiazolium mesitylenesulfonate;
2,3-diamino-6-chlorobenzothiazolium
2,6-diamino-benzothiazole dihydrochloride;
2,6-diamino-3-[2-(4-methoxyphenyl)-2-oxoethyl]benzothiazolium bromide;
2,6-diamino-3-[2-(3-methoxyphenyl)-2-oxoethyl]benzothiazolium bromide;
2,6-diamino-3-[2-(4-diethylaminophenyl)-2-oxoethyl]benzothiazolium bromide;
2,6-diamino-3-[2-(4-bromophenyl)-2-oxoethyl]benzothiazolium bromide;
2,6-diamino-3-[2-(2-phenyl)-2-oxoethyl]benzothiazolium bromide;
2,6-diamino-3-[2-(4-fluorophenyl-2-oxoethyl]benzothiazolium bromide;
3-acetamido-4-methyl-5-thiazolyl-ethyl acetate mesitylenesulfonate;
2,3-diamino-5-methylthiazolium mesitylenesulfonate;
3-[2-(2-naphthyl)-2-oxoethyl]-4-methyl-5-(2-hydroxyethyl)-thiazolium bromide;
3-[2-(3,5-di-tert-butyl-4-hydroxyphenyl)-2-oxoethyl]-4-methyl-5-(2-hydroxyethyl)thiazolium bromide;
3-[2-(2,6-dichlorophenethylamino)-2-oxoethyl]-4-methyl-5-(2-hydroxyethyl)thiazolium bromide;
3-[2-dibutylamino-2-oxoethyl]-4-methyl-5-(2-hydroxyethyl)thiazolium bromide;
3-[2-(4-carbethoxyanilino)-2-oxoethyl]-4-methyl-5-(2-hydroxyethyl)thiazolium bromide;
3-(2-(2,6-diisopropylanilino)-2-oxoethyl]-4-methyl-5-(2-hydroxyethyl)thiazolium bromide;
3-amino-4-methyl-5-[2-(2,6-dichlorobenzyloxy)ethyl]thiazolium mesitylenesulfonate;
3-[2-(4-carbmethoxy-3-hydroxyanilino)-2-oxoethyl]-4-methyl-5-(2-hydroxyethyl)thiazolium bromide;
2,3-diamino-4,5-dimethylthiazolium mesitylene sulfonate;
2,3-diamino-4-methyl-5-(2-hydroxyethyl)thiazolium mesitylene sulfonate;
2,3-diamino-5-(3,4-trimethylenedioxy phenyl)-thiazolium mesitylene sulfonate;
3-[2-(1,4-benzodioxan-6-yl)-2-oxoethyl]-4-methyl-5-(2-hydroxyethyl)thiazolium bromide;
3-[2-(3,4-trimethylenedioxyphenyl)-2-oxoethyl]-4-methyl-5-(2-hydroxyethyl)thiazolium bromide;
3-(2-[3,4-benzodioxan-6-yl]-2-oxoethyl)thiazolium bromide;
3-[2-(3,4-trimethylenedioxyphenyl)-2-oxoethyl]thiazolium bromide;
3-[2-(3,5-di-tert-butyl-4-hydroxyphenyl)-2-oxoethyl]thiazolium bromide;
3-[2-(3,5-di-tert-butyl-4-hydroxyphenyl)-2-oxoethyl]-4-methylthiazolium bromide;
3-[2-(3,5-di-tert-butyl-4-hydroxyphenyl)-2-oxoethyl]-5-methylthiazolium bromide;
3-[2-(3,5-di-tert-butyl-4-hydroxyphenyl)-2-oxoethyl]-4,5-dimethylthiazolium bromide;
3-[2-(3,5-di-tert-butyl-4-hydroxyphenyl)-2-oxoethyl]-benzothiazolium bromide;
1-methyl-3-[2-(3,5-di-tert-butyl-4-hydroxyphenyl)-2-oxoethyl]imidazolium bromide;
3-[2-(4-n-pentylphenyl)-2-oxoethyl]thiazolium bromide;
3-[2-(4-n-pentylphenyl)-2-oxoethyl]-4-methyl-5-(2-hydroxyethyl)thiazolium bromide;
3-[2-(4-diethylaminophenyl)-2-oxoethyl]-4-methyl-5-(2-hydroxyethyl)thiazolium bromide;
3-(2-phenyl-2-oxoethyl)-4-methyl-5-vinylthiazolium bromide;
3-[2-(3,5-tert-butyl-4-hydroxyphenyl)-2-oxoethyl)-4-methyl-5-vinylthiazolium bromide;
3-(2-tert-butyl-2-oxoethyl)thiazolium bromide
3-(2-tert-butyl-2-oxoethyl)-4-methyl-5-(2-hydroxyethyl)thiazolium bromide;
3-(3'-methoxybenzyl)-4-methyl-5-(2-hydroxyethyl)thiazolium chloride;
3-(2,6-dichlorobenzyl)-4-methyl-5-(2-hydroxyethyl)thiazolium chloride;
3-(2-nitrobenzyl)-4-methyl-5-(2-hydroxyethyl)thiazolium bromide;
3[2-(4-chlorophenyl)-2-oxoethyl]thiazolium bromide;
3[2-(4-chlorophenyl)-2-oxoethyl]-4-methyl-5-(2-hydroxyethyl)thiazolium bromide
3[2-(4-methoxyphenyl)-2-oxoethyl]-4-methyl-5-(2-hydroxyethyl)thiazolium bromide.
3-[2-(3-phenyl-5-isoxazolyl)-2-oxoethyl]thiazolium bromide
3-[2-(3-phenyl-5-isoxazolyl)-2-oxoethyl]-4,5-dimethylthiazolium bromide
3-[2-(3-phenyl-5-isoxazolyl)-2-oxoethyl]-4-methyl-5-(2-hydroxyethyl)thiazolium bromide
3-[2-[4-(2-ethoxy-2-oxoethyl)-2-thiazolyl]amino-2-oxoethyl]-4,5-dimethylthiazolium chloride
3-[2-(3-phenyl-5-isoxazolyl)-2-oxoethyl]-4-methyl-5-(6-hydroxyhexyl)thiazolium bromide
3-[2-(2,6-dimethyl-4-morpholinyl)-2-oxoethyl]-4,5-dimethylthiazolium bromide
3-(2-(1-piperidinyl)-2-oxoethyl)-4,5-dimethylthiazolium bromide
3-(2-(2-furanyl)-2-oxoethyl)-4,5-dimethylthiazolium bromide
3-(2-(2-furanyl)-2-oxoethyl)-4-(2-hydroxypentyl)thiazolium bromide
3-[2-(2-oxo-1,2,3,4-tetrahydro-6-quinolinyl)-2-oxoethyl]-4,5-dimethylthiazolium bromide
3-(2-(1-pyrrolidinyl)-2-oxoethyl)-4,5-dimethylthiazolium bromide
3-[2-(3-methyl-2-thianaphthenyl)-2-oxoethyl]-4,5-dimethylthiazolium bromide
3-[2-(4-phenyl-1-piperazinyl)-2-oxoethyl]-4,5-dimethylthiazolium bromide
3-(2-(2-thienyl)-2-oxoethyl)-4,5-dimethylthiazolium bromide
3-(2-(2-thienyl)-2-oxoethyl)-4-methyl-5-hydroxyethylthiazolium bromide
3-(2-(4-thiomorpholinyl)-2-oxoethyl)-4,5-dimethylthiazolium bromide
3-(2-(hexahydro-1-azepinyl)-2-oxoethyl)-4,5-dimethylthiazolium bromide
3-[2-(4-[2-methoxyphenyl]-1-piperazinyl)-2-oxoethyl]-4,5-dimethylthiazolium chloride
3-(2-(octahydro-1-azocinyl)-2-oxoethyl)-4,5-dimethylthiazolium bromide
3-(2-(2-pyridinyl)-2-oxoethyl)-4,5-dimethylthiazolium bromide
3-[2-(2-methyl-1-piperidinyl)-2-oxoethyl]-4,5-dimethylthiazolium chloride 3-[2-(2,6-dimethyl-1-piperidinyl)-2-oxoethyl]-4,5-dimethylthiazolium chloride
3-[2-(4-benzyl-1-piperidinyl)-2-oxoethyl]-4,5-dimethylthiazolium chloride
3-[2-(4-benzyl-1-piperazinyl)-2-oxoethyl]-4,5-dimethylthiazolium chloride
3-[2-(3-phenyl-5-isoxazolyl)-2-oxoethyl]-4-octylthiazolium bromide
3-(2-(4-morpholinyl)-2-oxoethyl)-4,5-dimethylthiazolium bromide
3-[2-[4-(2-ethoxy-2-oxoethyl)-2-thiazolyl]amino-2-oxoethyl]-4,5-dipropylthiazolium chloride
3-(2-(4-morpholinyl)-2-oxoethyl)-4,5-dioctadecylthiazolium bromide
3-[2-(2,6-dimethyl-4-morpholinyl)-2-oxoethyl]-4,5-dipentylthiazolium bromide
3-(2-(1-piperidinyl)-2-oxoethyl)-4,5-didodecylthiazolium bromide
3-(2-(2-furanyl)-2-oxoethyl)-5-decylthiazolium bromide
3-[2-(2-oxo-1,2,3,4-tetrahydro-6-quinolinyl)-2-oxoethyl]-4,5-dioctylthiazolium bromide
3-(2-(1-pyrrolidinyl)-2-oxoethyl)-4,5-diethylthiazolium bromide
3-[2-(3-methyl-2-thianaphthenyl)-2-oxoethyl]-4,5-dipentylthiazolium bromide
3-[2-(4-phenyl-1-piperazinyl)-2-oxoethyl]thiazolium bromide
3-(2-(2-thienyl)-2-oxoethyl)thiazolium bromide
3-(2-(2-thienyl)-2-oxoethyl)-4-methyl-5-(6-hydroxyhexyl)thiazolium bromide
3-(2-(4-thiomorpholinyl)-2-oxoethyl)thiazolium bromide
3-(2-(hexahydro-1-azepinyl)-2-oxoethyl)-4,5-dioctylthiazolium bromide
3-(2-(octahydro-1-azocinyl)-2-oxoethyl)-4,5-didecylthiazolium bromide
3-(2-(2-pyridinyl)-2-oxoethyl)-4,5-dioctylthiazolium bromide
3-[2-(2-methyl-1-piperidinyl)-2-oxoethyl]-4,5-dipropylthiazolium chloride
3-[2-(2,6-dimethyl-1-piperidinyl)-2-oxoethyl]-4-methylthiazolium chloride
3-[2-(4-benzyl-1-piperidinyl)-2-oxoethyl]-5-methylthiazolium chloride
3-[2-(4-benzyl-1-piperazinyl)-2-oxoethyl]-4-octylthiazolium chloride
1-methyl-3-[2-(3-methoxyphenyl)-2-oxoethyl]imidazolium bromide;
1-methyl-3-[2-(4-methoxyphenyl)-2-oxoethyl]imidazolium bromide;
1-methyl-3-[2-(2,4-dimethoxyphenyl)-2-oxoethyl]imidazolium bromide;
1-methyl-3-[2-(4-diethylaminophenyl)-2-oxoethyl]imidazolium bromide;
1-methyl-3-[2-amino-2-oxoethyl]imidazolium bromide;
1-methyl-2-amino-imidazolium mesitylene sulfonate;
1-methyl-3-[2-phenyl-2-oxoethyl]imidazolium bromide;
3-amino-1-(ethoxycarbonylpentyl)imidazolium mesitylenesulfonate;
1-(ethoxycarbonylpentyl)-3-[2-(3-methoxyphenyl)-2-oxoethyl]imidazolium bromide;
1-methyl-3-[2-(4-bromophenyl)-2-oxoethyl]imidazolium bromide;
1-methyl-3-[2-(4-fluorophenyl)-2-oxoethyl]imidazolium bromide;
1-methyl-3-[2-(3,4-difluorophenyl)-2-oxoethyl]imidazolium bromide;
1-(ethoxycarbonylpentyl)-3-[2-(4-methoxyphenyl)-2-oxoethyl]imidazolium bromide;
1-(4-acetylphenyl)-3-amino-imidazolium mesitylenesulfonate;
1-(ethoxycarbonylpentyl)-3-[2-(4-methoxyphenyl)-2-oxoethyl]imidazolium bromide;
1-(ethoxycarbonylpentyl)-3-[2-(4-methylphenyl)-2-oxoethyl]imidazolium bromide;
1-amino-3-benzoyl-imidazolium mesitylene sulfonate;
1-methyl-3-(2-naphth-2-yl-2-oxoethyl)imidazolium bromide;
1-methyl-3-[(4-biphen-1-yl)-2-oxoethyl]imidazolium bromide;
1-methyl-3-[(3-trifluoromethylphenyl)-2-oxoethyl)]imidazolium bromide;
1-methyl-3-[4-(2,4-difluorophenyl)-2-oxoethyl]imidazolium chloride;
3-[2-(thien-2-yl)-2-oxoethyl]-1-methyl-5-imidazolium bromide;
1-methyl-3-[2-(2,4,6-trimethylphenyl)-2-oxoethyl]imidazolium bromide;
1-methyl-3-[2-(2,4-dichlorophenyl)-2-oxoethyl]imidazolium chloride;
3-(2-phenyl-2-oxoethyl)-1-phenylimidazolium chloride;
3-(2-phenyl-2-oxoethyl)-1-ethylimidazolium chloride;
3-(2-phenyl-2-oxoethyl)-1-butylimidazolium chloride;
3-(2-phenyl-2-oxoethyl)-1-allylimidazolium chloride;
3-(2-trifluoromethylphenyl-2-oxoethyl)-4,5-dimethylthiazolium bromide;
3-(2-trifluoromethylphenyl-2-oxoethyl)-4-methyl-5-(2-hydroxyethyl)thiazolium bromide;
3-(2-trifluoromethylphenyl-2-oxoethyl)-1-methylimidazolium bromide;
3-(2-trifluoromethylphenyl-2-oxoethyl)-1-methylimidazolium bromide;
1-butyl-3-amino-imidazolium-mesitylenesulfonate;
3-[2-(thien-2-yl)-2-oxoethyl]-1,2-dimethylimidazolium bromide;
3-[2-(pyrrolidin-1-yl)-2-oxoethyl]-1,2-dimethylimidazolium chloride;
3-(2-phenyl-2-oxoethyl)-1,2-dimethylimidazolium chloride;
3-amino-1,2-dimethylimidazolium mesitylenesulfonate;
3-[2-(pyrrolidin-1-yl)-2-oxoethyl]-1-ethylimidazolium chloride;
3-[2-(pyrrolidin-1-yl)-2-oxoethyl]-1-phenylimidazolium chloride;
3-[2-(pyrrolidin-1-yl)-2-oxoethyl]-1-methylimidazolium chloride;
3-[2-(thien-2-yl)-2-oxoethyl]-1-ethylimidazolium bromide;
3-[2-(thien-2-yl)-2-oxoethyl]-1-phenylimidazolium bromide;
3-[2-(thien-2-yl-2-oxoethyl]-1,4,5-trimethylimidazolium bromide;
3-[2-(pyrrolidin-2-yl)-2-oxoethyl]-1,4,5-trimethylimidazolium chloride;
3-[2-(4-chlorophenyl)-2-oxoethyl]-1,2-dimethylimidazolium bromide;
3-[2-(4-bromophenyl)-2-oxoethyl]-1,2-dimethylimidazolium bromide;
3-[2-(4-fluorophenyl)-2-oxoethyl]-1,2-dimethylimidazolium bromide;
3-[2-(2,4-difluorophenyl)-2-oxoethyl]-1,2-dimethylimidazolium chloride;
3-[2-(2,4-dichlorophenyl)-2-oxoethyl]-1,2-dimethylimidazolium chloride;
3-[2-(3,4-difluorophenyl)-2-oxoethyl]-1,2-dimethylimidazolium bromide;

3-[2-(2-methoxyphenyl)-2-oxoethyl]-1,2-dimethylimidazolium bromide;
3-[2-(3-methoxyphenyl)-2-oxoethyl]-1,2-dimethylimidazolium bromide;
3-[2-(4-methoxyphenyl)-2-oxoethyl]-1,2-dimethylimidazolium bromide;
3-[2-(2,4-dimethoxyphenyl)-2-oxoethyl]-1,2-dimethylimidazolium bromide;
3-[2-(2,5-dimethoxyphenyl)-2-oxoethyl]-1,2-dimethylimidazolium bromide;
3-[2-(2,4,6-trimethylphenyl)-2-oxoethyl]-1,2-dimethylimidazolium bromide;
3-[2-(4-methylphenyl)-2-oxoethyl]-1,2-dimethylimidazolium bromide;
3-[2-(4-diethylaminophenyl)-2-oxoethyl]-1,2-dimethylimidazolium bromide;
3-[2-amino-2-oxoethyl]-1,2-dimethylimidazolium bromide;
3-[2-(3,5-di-tert-butyl-4-hydroxyphenyl)-2-oxoethyl]-1,2-dimethylimidazolium bromide;
3-[2-(3,4-trimethylenedioxyphenyl)-2-oxoethyl]-1,2-dimethyl-imidazolium bromide;
3-[2-(4-biphenyl)-2-oxoethyl]-1,2-dimethylimidazolium bromide;
3-[2-(3,5-dichloroanilino)-2-oxoethyl]-1,2-dimethylimidazolium bromide;
3-[2-(4-trifluoromethylphenyl)-2-oxoethyl]-1,2-dimethylimidazolium bromide;
3-[2-(2,6-dichlorophenyl)-2-oxoethyl]-1,2-dimethylimidazolium bromide;
3-[2-(thiomorpholin-4-yl)-2-oxoethyl]-1,2-dimethylimidazolium chloride;
3-[2-(morpholin-4-yl)-2-oxoethyl]-1,2-dimethylimidazolium chloride;
3-[2-(piperidin-1-yl)-2-oxoethyl]-1,2-dimethylimidazolium chloride;
3-[2-hexamethyleneimino-2-oxoethyl]-1,2-dimethylimidazolium chloride;
3-[2-heptamethyleneimino-2-oxoethyl]-1,2-dimethylimidazolium chloride;
3-[2-naphthyl-2-oxoethyl]-1,2-dimethylimidazolium bromide;
3-[2-(2-trifluoromethylphenyl)-2-oxoethyl]-1,2-dimethylimidazolium bromide;
3-[2-(2-trifluoromethylphenyl)-2-oxoethyl]-2,4,5-trimethylthiazolium bromide;
3-(2-methyl-2-oxoethyl)-1,2-dimethylimidazolium chloride;
3-(2-phenyl-2-oxoethyl)-2-amino-1-methylbenzimidazolium chloride;
3-[2-(thiomorpholin-4-yl)-2-oxoethyl]-1-methylimidazolium chloride;
3-[2-(4-phenylpiperazin-1-yl)-2-oxoethyl]-1,2-dimethylimidazolium chloride;
3-[2-(4-benzylpiperazin-1-yl)-2-oxoethyl]-1,2-dimethylimidazolium chloride;
3-[2-{6-(1,2,3,4-tetrahydro-1,1,4,4-tetramethyl-naphthalyl)}-2-oxoethyl]-1,2-dimethylimidazolium bromide;
3-[2-(1,4-benzodioxan-6-yl)-2-oxoethyl]-1,2-dimethylimidazolium bromide;
3-[2-(phenyl)-2-oxoethyl]-5-chloro-3-methyl-1-ethylimidazolium chloride;
3-[2-(phenyl)-2-oxoethyl]-4-methyl-2-ethylthiazolium chloride;
3-(2-phenyl-2-oxoethyl)-1-methyl-2-aminoimidazolium chloride;
3-[2-(pyrrolidin-2-yl)-2-oxoethyl]-2-amino-1-methylimidazolium chloride;
3-(2-phenyl-2-oxoethyl)-1,2-dimethyl-5-nitroimidazolium chloride;
3-[2-(4-acetylanilino)-2-oxoethyl]-1,2-dimethylimidazolium chloride;
3-[2-(4-carboethoxyanilino)-2-oxoethyl]-1,2-dimethylimidazolium chloride;
3-[2-(2,6-diisopropylanilino)-2-oxoethyl]-1,2-dimethylimidazolium bromide;
3-[2-anilino-2-oxoethyl]-1,2-dimethylimidazolium chloride;
3-[(4-bromoanilino)-2-oxoethyl]-1,2-dimethylimidazolium chloride;
3-[2-(4-[morpholin-4-yl]phenyl)-2-oxoethyl]-1,2-dimethylimidazolium bromide;
3-[2-dibutylamino-2-oxoethyl]-1,2-dimethylimidazolium chloride;
3-[2-(2,6-dichloro-phenethylamino)-2-oxoethyl]-1,2-dimethylimidazolium;
3-[2-(3-hydroxy-4-methoxycarbonylanilino)-2-oxoethyl]-1,2-dimethylimidazolium bromide;
3-[2-cyclopentylamino-2-oxoethyl]-1,2-dimethylimidazolium chloride;
3-[2-neopentylamino-2-oxoethyl]-1,2-dimethylimidazolium chloride;
3-[2-(pyridin-2-yl)-2-oxoethyl]-4,5-dimethylimidazolium bromide;
3-(2-phenyl-2-oxoethyl)-1,4,5-trimethylimidazolium chloride;
3-(2-phenyl-2-oxoethyl)-1,2,4,5-tetramethylimidazolium chloride;
3-[2-(6-[1,2,3,4-tetrahydroquinolinyl])-2-oxoethyl]-1,2-dimethylimidazolium chloride;
3-[2-(2,6-difluorophenyl)-2-oxoethyl]-1,2-dimethylimidazolium bromide;
1-vinyl-3-[2-phenyl-2-oxoethyl]imidazolium chloride;
1-(4-hydroxyphenyl)-3-(2-phenyl-oxoethyl)imidazolium chloride;
1-(4-acetylphenyl)-3-(2-phenyl-2-oxoethyl)imidazolium chloride;
1-methyl-3-(2-phenyl-2-oxoethyl)benzimidazolium chloride;
1,5-dicyclohexyl-3-(2-phenyl-2-oxoethyl)imidazolium chloride;
1-(4-methoxycarbonylphenyl)-3-(2-phenyl-2-oxoethyl)imidazolium chloride;
1-benzyl-3-(2-phenyl-2-oxoethyl)imidazolium chloride;
1-(4-methoxyphenyl)-3-(2-phenyl-2-oxoethyl)imidazolium chloride;
3-[2-(tert-butylamino)-2-oxoethyl]-1,2-dimethylimidazolium chloride;
3-[2-(2,4-difluoroanilino)-2-oxoethyl]-1,2-dimethylimidazolium chloride;
3-[2-(2,4,6-trimethylanilino)-2-oxoethyl]-1,2-dimethylimidazolium chloride;
3-(2-cyclohexylamino-2-oxoethyl)-1,2-dimethylimidazolium chloride;
3-[2-(4-carboxy-3'-hydroxyanilino)-2-oxoethyl)-1,2-dimethylimidazolium chloride;
3-[2-([2-morpholin-4-yl]ethylamino)-2-oxoethyl]-1,2-dimethylimidazolium chloride;
3-[2-(3-[2-methylpiperidin-1-yl]propylamino)-2-oxoethyl]-1,2-dimethylimidazolium chloride;
3-(2-veratrylamino-2-oxoethyl)-1,2-dimethylimidazolium chloride;
3-[2-(thiazolidin-3-yl)-2-oxoethyl]-1,2-dimethylimidazolium chloride;
3-[2-(1-adamantanamino)-2-oxoethyl]-1,2-dimethylimidazolium chloride, 3-[2-(2-adamantanamino)-2-oxoethyl]-1,2-dimethylimidazolium chloride;
3-[2-(2-indanylamino)-2-oxoethyl]-1,2-dimethylimidazolium chloride;
3-[2-(2'-[3"-chlorobenzoyl]-5-chloroanilino)-2-oxoethyl]-1,2-dimethylimidazolium chloride;
3-[2-(4-ethoxycarbonylthiazol-2-yl)amino-2-oxoethyl]-1,2-dimethylimidazolium chloride;
3-(cyclohexylamino-2-oxoethyl)-2,4,5-trimethylthiazolium chloride;
3-[2-(2-chloroanilino)-2-oxoethyl]-1,2-dimethylimidazolium bromide;
3-[2-(2-chloroanilino)-2-oxoethyl]-2,4,5-trimethylthiazolium bromide;
3-[2-(3,4-dimethoxyphenethylamino)-2-oxoethyl]-1,2-dimethylimidazolium chloride;
3-[2-(2,4-dichloroanilino)-2-oxoethyl]-1,2-dimethylimidazolium chloride;
3-[2-(2,6-dichloroanilino)-2-oxoethyl]-1,2-dimethylimidazolium chloride;
3-[(2-pyrrolidin-1-yl)-2-oxoethyl]-1,2,4,5-tetramethylimidazolium chloride;
3-[2-(4-[pyrrolidin-1-yl]piperidin-1-yl)-2-oxoethyl]-1,2-dimethylimidazolium chloride;
3-[2-(4-[piperidin-1-yl]piperidin-1-yl)-2-oxoethyl]-1,2-dimethylimidazolium chloride;
3-[2-(2,6-difluoroanilino)-2-oxoethyl]-1,2-dimethylimidazolium chloride;
3-(2-cyclobutylamino-2-oxoethyl)-1,2-dimethylimidazolium chloride;
3-[2-(3,5-difluoroanilino)-2-oxoethyl]-1,2-dimethylimidazolium chloride;
3-[2-(2-fluoroanilino)-2-oxoethyl]-1,2-dimethylimidazolium chloride;
3-[2-(1R,2R,3R,5S-isopinocampheylamino)-2-oxoethyl]-1,2-dimethylimidazolium chloride;
3-[2-(1,3,3-trimethyl-6-azabicyclo-[3,2,1]octanyl)-2-oxoethyl]-1,2-dimethylimidazolium chloride;
3-[2-(6,7-dimethoxy-1,2,3,4-tetrahydroisoquinolin-2-yl)-2-oxoethyl]-1,2-dimethylimidazolium chloride;
3-[2-(1,2,3,4-tetrahydro-1-naphthylamino)-2-oxoethyl]-1,2-dimethylimidazolium chloride;
1-(4-methoxyphenyl)-3-aminoimidazolium mesitylenesulfonate;
1-benzyl-3-aminoimidazolium mesitylenesulfonate;
1-vinyl-3-aminoimidazolium mesitylenesulfonate;
1-methyl-3-aminoimidazolium mesitylenesulfonate;
1-(4-methoxycarbonylphenyl)-3-aminoimidazolium mesitylenesulfonate;
3-(2-phenyl-2-hydroxyethyl)-4,5-dimethylthiazolium chloride;
S(−) 3-(2-Phenyl-2-hydroxyethyl)-4,5-dimethylthiazolium chloride;
R(−) 3-(2-Phenyl-2-hydroxyethyl)-4,5-dimethylthiazolium chloride;
3-[2-(2-Hydroxyphenyl)-2-oxoethyl]-4,5-dimethylthiazolium bromide;
3-[2-(3-Hydroxyphenyl)-2-oxoethyl]-4,5-dimethylthiazolium bromide;
3-[2-(4-Hydroxyphenyl)-2-oxoethyl]-4,5-dimethylthiazolium bromide bromide;
3-(2-phenyl-2-oxoethyl)-4-methyl-5-(hydroxymethyl)-thiazolium chloride;
3-[2-(2,4-dihydroxyphenyl)-2-oxoethyl]-4,5-dimethylthiazolium bromide;
3-[2-(3,5-dihydroxyphenyl)-2-oxoethyl]-4,5-dimethylthiazolium bromide;
3-[2-(2,5-dihydroxyphenyl)-2-oxoethyl]-4,5-dimethylthiazolium bromide;
3-[2-(3,4-dihydroxyphenyl)-2-oxoethyl]-4,5-dimethylthiazolium chloride;
3-[2-(2,3-dihydroxyphenyl)-2-oxoethyl]-4,5-dimethylthiazolium;
thiamine hydrochloride;
(1-ethyl-hexanoate)-3-[2-(4-chlorophenyl)-2-oxoethyl]imidazolium bromide;
3-[2-[6-[1,2,3,4-tetrahydro-1,1,4,4-tetramethyl-naphthalyl]]-2-oxoethyl]thiazolium bromide;
3-[2-(3,5-dichloroanilino)-2-oxoethyl]thiazolium bromide;
3-[2-(4-biphenyl)-2-oxoethyl]thiazolium bromide;
Carboxylates (diphosphate ester of thiamine HCl);
monophosphate ester of thiamine HCl;
3-[2-(9H-fluoren-2-yl)-2-oxoethyl]-4,5-dimethylthiazolium bromide;
3-[2-{6-(1,2,3,4-tetrahydro-1,1,4,4-tetramethyl-naphthalyl)}-2-oxoethyl]-4,5-dimethylthiazolium bromide;
3-[2-{5-(3-phenylisoxazolyl)}-2-oxoethyl]-4,5-dimethylthiazolium bromide;
3-[2-(4-biphenyl)-2-oxoethyl]-4,5-dimethylthiazolium bromide;
3-[2-(3,5-dichloroanilino)-2-oxoethyl]-4,5-dimethylthiazolium bromide;
3-[2-{6-[1,2,3,4-tetrahydro-1,1,4,4-tetramethyl-naphthalyl]}-2-oxoethyl]-4-methyl-5-(2-hydroxyethyl)thiazolium bromide;
3-[2-(3-phenylisoxazol-5-yl)-2-oxoethyl]-4-methyl-5-(2-hydroxyethyl)thiazolium bromide;
3-[2-(4-biphenyl)-2-oxoethyl]-4-methyl-5-(2'-hydroxyethyl)thiazolium bromide;
3-[2-(3,5-dichloroanilino)-2-oxoethyl]-4-methyl-5-(2-hydroxyethyl)thiazolium bromide;
3-{[2-(3-methoxybenzoyl)amino]benzyl}-4,5-dimethylthiazolium bromide;
3-[2-(2-amino-5-carboethoxymethylene-thiazolyl)-2-oxoethyl]-4,5-dimethylthiazolium chloride;
3-[2-(morpholin-4-yl-2-oxoethyl]-4,5-dimethylthiazolium bromide;
3-[2-(2,6-dimethylmorpholin-4-yl)-2-oxoethyl]-4,5-dimethylthiazolium bromide;
3-[2-(piperidin-1-yl)-2-oxoethyl]-4,5-dimethylthiazolium bromide;
3-[2-(fur-2-yl)-2-oxoethyl]-4,5-dimethylthiazolium bromide;
3-[2-[6-(2-oxo-1,2,3,4-tetrahydroquinolinyl)]-2-oxoethyl]-4,5-dimethylthiazolium bromide;
3-[2-(pyrrolidin-1-yl)-2-oxoethyl]-4,5-dimethylthiazolium bromide;
3-[2-(4-carboxyanilino)-2-oxoethyl)-4,5-dimethylthiazolium chloride;
3-[2-(2-{3-methylbenzo[b]thienyl})-2-oxoethyl]-4,5-dimethylthiazolium bromide;
3-[2-(4-phenylpiperazin-1-yl)-2-oxoethyl]-4,5-dimethylthiazolium bromide;
3-[2-(4-fluorophenyl)-2-oxoethyl]-4,5-dimethylthiazolium bromide;
3-[2-(4-methoxyphenyl)-2-oxoethyl]-4,5-dimethylthiazolium bromide;
3-[2-(4-trifluoromethyl)-2-oxoethyl]-4,5-dimethyl-thiazolium bromide;
3-[2-(2,4-difluorophenyl)-2-oxoethyl]-4,5-dimethylthiazolium bromide;
3-[2-(2,4,6-trimethylphenyl)-2-oxoethyl]-4,5-dimethylthiazolium chloride;

3-[2-tert-butyl-2-oxoethyl]-4,5-dimethylthiazolium chloride;
3-[2-(2,4-dichlorophenyl)-2-oxoethyl]-4,5-dimethylthiazolium chloride;
3-[2-(4-Diethylaminophenyl)-2-oxoethyl]-4,5-dimethylthiazolium chloride;
3-(2-methyl-2-oxoethyl)-4,5-dimethylthiazolium chloride;
3-[2-(2,6-dichlorophenyl)-2-oxoethyl]-4,5-dimethylthiazolium chloride;
3-(2-phenyl-2-oxoethyl)-4-phenylthiazolium chloride;
3-[2-(2,4-dichlorophenyl)-2-oxoethyl]-4-phenylthiazolium chloride;
3-[2-(2,4,6-trimethylphenyl)-2-oxoethyl]-4-phenylthiazolium bromide;
3-(2-methyl-2-oxoethyl)-4-methyl-5-(hydroxyethyl) thiazolium chloride;
3-[2-(2,4-dichlorophenyl)-2-oxoethyl]-4-methyl-5-(2-hydroxyethyl)thiazolium;
3-[2-(2,4,6-trimethylphenyl)-2-oxoethyl]-4-methyl-5-(2-hydroxyethyl)thiazolium chloride;
3-(1-methyl-2-phenyl-2-oxoethyl)-4,5-dimethylthiazolium chloride;
3-(phenylthiomethyl)-4,5-dimethylthiazolium chloride;
3-[2-(thien-2-yl)-2-oxoethyl]-4,5-dimethylthiazolium bromide;
3-[2-(2-thien-2-yl)-2-oxoethyl]-4-methyl-5-(2-hydroxyethyl)thiazolium bromide;
3-[2-phenyl-2-oxoethyl]-4,5-cyclohexenyl-thiazolium bromide;
3-[2-(2,4-dichlorophenyl)-2-oxoethyl]-4,5-cyclohexenothiazolium chloride;
3-(2-phenyl-2-oxoethyl)-4,5-cyclopenteno-thiazolium bromide;
3-[2-(2,4-dichlorophenyl)-2-oxoethyl]-4,5-cyclopentenothiazolium chloride;
3-[2-(2,4,6-trimethylphenyl)-2-oxoethyl]-4,5-cyclopentenothiazolium bromide;
3-[2-(2,4,6-trimethylphenyl)-2-oxoethyl]-4,5-cyclopentenothiazolium bromide;
3-(2-cyanomethyl)-4,5-cyclohexeno-thiazolium bromide;
3-(2-cyanomethyl)-4,5-cyclopenteno-thiazolium bromide;
3-(2-cyanomethyl)-4,5-dimethyl-thiazolium bromide;
3-(2-methyl-2-oxoethyl)-4,5-cyclopenteno-thiazolium chloride;
3-(2-cyanomethyl)-4-methyl-5-(2-hydroxyethyl)thiazolium bromide;
3-(2-phenyl-2-oxoethyl)-4-methyl-5-(hydroxyethylsuccinyl)thiazolium chloride;
3-[2-(thien-2-yl)-2-oxoethyl]-2,4,5-trimethylthiazolium bromide;
3-amino-4-methyl-5-(2-hydroxyethyl)-thiazolium bromide;
3-(2-phenyl-2-oxoethyl)-2,4,5-trimethylthiazolium chloride;
3-amino-2,4,5-trimethylthiazolium mesitylenesulfonate;
3-[2-(4-{2-methoxyphenyl}piperazin-1-yl)-2-oxoethyl]-4,5-dimethylthiazolium chloride;
3-[2-hydroxy-2-oxoethyl]-4,5-dimethylthiazolium chloride;
3-(2-phenyl-2-oxoethyl)-2-aminothiazolium chloride;
3-[2-(thiomorpholin-4-yl)-2-oxoethyl]-5-hydroxyethyl-4-methylthiazolium chloride;
3-[2-(4-trifluoromethylphenyl)-2-oxoethyl]-2,4,5-trimethylthiazolium bromide;
3-[2-phenyl-2-oxoethyl]-2-isobutylthiazolium chloride;
3-[2-(thiomorpholin-4-yl)-2-oxoethyl]-2,4,5trimethylthiazolium chloride;
3-(2-amino-2-oxoethyl)-2-methylbenzothiazolium chloride;
3-[2-(4-acetanilino)-2-oxoethyl]-2,4,5-trimethylthiazolium chloride;
3-[2-(4-carboethoxyanilino)-2-oxoethyl]-2,4,5-trimethylthiazolium bromide;
3-[2-(2,6-diisopropylanilino)-2-oxoethyl]-2,4,5-trimethylthiazolium bromide;
3-[(4-bromoanilino)-2-oxoethyl]-2,4,5-trimethylthiazolium chloride;
3-[2-(2-naphthyl)-2-oxoethyl]-4,5-dimethylthiazolium bromide;
3-[2-([3-phenylisoxazol-5-yl])-2-oxoethyl]thiazolium bromide;
3-methyl-4,5-dimethythiazolium chloride;
3-ethyl-4,5-dimethylthiazolium bromide;
3-[2-(4'-acetoxyphenyl)-2-oxoethyl]-4,5-dimethylthiazolium bromide;
3-[2-phenyl-2-oxoethyl]-4-methyl-5-(ethoxycarbonyl)thiazolium chloride;
3-[2-(4-diethylaminophenyl)-2-oxoethyl]thiazolium chloride;
1-methyl-3-(2-cyanomethyl)imidazolium bromide;
3-(2-cyanomethyl)-4,5-dimethylthiazolium bromide;
3-(2-cyanomethyl)-4,5-cyclopentenothiazolium bromide,
3-(2-cyanomethyl)-4,5-cyclohexenothiazolium bromide;
1-methyl-3-(2-cyanomethyl)imidazolium bromide;
1-vinyl-3-(2-cyanomethyl)imidazolium chloride;
1-allyl-3-(2-cyanomethyl)imidazolium chloride;
1-(4-acetylphenyl)-3-(2-cyanomethyl)imidazolium chloride;
1-phenyl-3-(2-cyanomethyl)imidazolium chloride;
1-(4-methoxyphenyl)-3-(2-cyanomethyl)imidazolium chloride;
1-(4-methoxycarbonylphenyl)-3-(2-cyanomethyl-imidazolium chloride;
3-(2-cyanomethyl)-1-methylbenzimidazolium chloride;
1,5-dicyclohexyl-3-(2-cyanomethyl)imidazolium bromide;

as well as other biologically or pharmaceutically acceptable salts thereof.

Compounds of the general formula I wherein the $R^1$, $R^2$, X, Y, and Z are defined as above can be prepared by the methods of U.S. Pat. Nos. 5,656,261; 5,853,703; and 6,007,865; or as described below. Moreover, certain of the compounds are conveniently prepared by chemical syntheses that are well-known in the art. In addition, certain of the compounds are well-known and readily available from chemical supply houses or can be prepared by synthetic methods specifically published therefor. The chemical reagents shown in the schemes below provide nonlimiting examples of means well known in the art to carry out the reaction steps shown.

Compounds of the invention wherein Y is $CH(R^5)$—C(O)—$R^7$ can be prepared according to the synthetic route depicted in Scheme 1 (wherein $R^1$, $R^2$, $R^5$, $R^7$, M, Q, and Z are as described above, and X is a halide). An acetyl derivative with a suitable a α leaving group, for example, an α-halo acetyl derivative, can be used to alkylate a suitably substituted thiazole, oxazole, or imidazole. The alkylation reaction may be conducted at elevated temperatures in a suitable solvent, for example, acetonitrile or ethanol, or without solvent.

Scheme 1

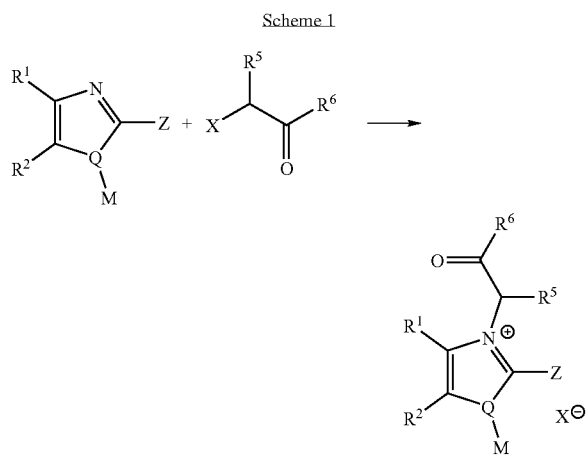

Compounds of the invention wherein $R^6$ is a group of the formula —CH(OH)Rs may be prepared as shown in Schemes 2 and 3 (see below). In the nonlimiting exemplary synthetic schemes below, some product compounds are shown as specific optical isomers and others are shown as racemic compounds. One skilled in the art will appreciate that appropriate reaction conditions and reagents, that are well known in the art, can be used to customize the degree of reaction stereoselectivity. Thus, isolated stereoisomers are within the scope of compounds of the invention. For example, compound 2 can be obtained as a racemic mixture from compound 1 or as an S (compound 2a) or R stereoisomer depending on the reducing agent employed. Substitution of comparable reagents to achieve different stereoselectivity, even when not shown explicitly by the scheme, is well known in the art at the time of filing. Moreover, synthetic processes and stereoselective purifications, such as chromatography on stereoselective media can be used to achieve 90%, 95%, 98%, 99% or better isomeric purity, such that compositions substantially free of the non-desired isomer can be prepared.

A synthetic scheme for making compounds of the formula I wherein Y is CH$_2$CH(OH)Rs is shown in Scheme 2. A hydroxyl is incorporated into a nucleophile used to derivatize a thiazole compound, as follows:

Scheme 2

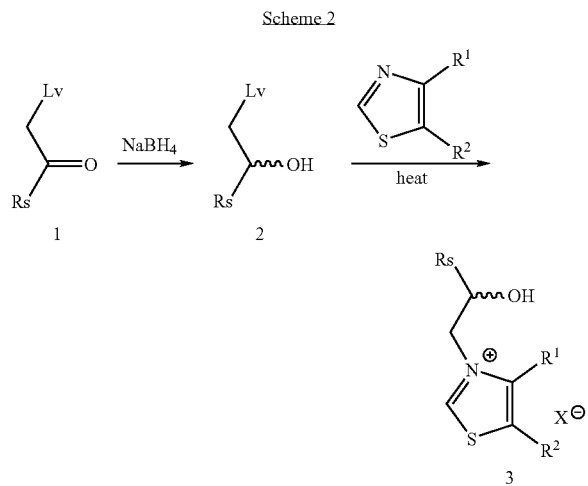

where Lv is a leaving group such as chloro. In a related synthesis, Compound 1 is reduced with a stereoselective reducing agent such as (−) DIP-chloride [(−)-B-chlorodiisopinocampheylborane] or (+) DIP-chloride [(+)-B-chlorodiisopinocampheylborane]. For example:

Scheme 3

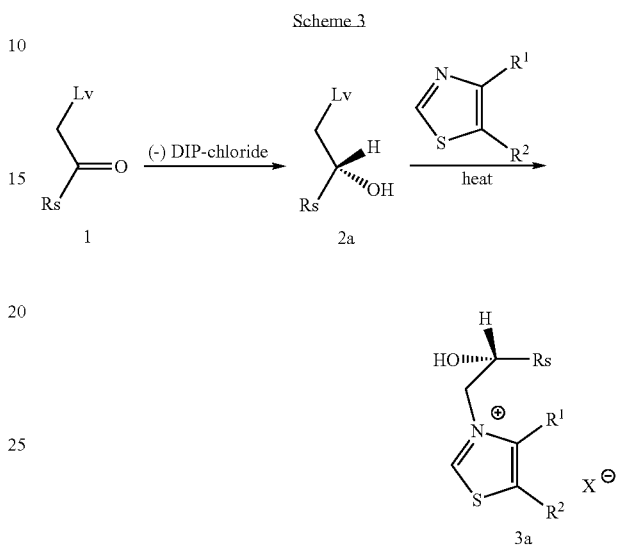

Substitution of (+) DIP-chloride results predominately in the mirror image to compound 3a.

Scheme 4 exemplifies methods of preparing compounds of the formula I wherein Y is a group of the formula —CH$_2$R$^6$ wherein R$^6$ is a substituted or unsubstituted benzoyl moiety. In this particular preparation, acetophenones substituted in the phenyl moiety with hydroxy groups are derivatized to add a leaving group to the alpha methyl group, and the resulting intermediate is then used to alkylate thiazoles, as exemplified below:

Scheme 4

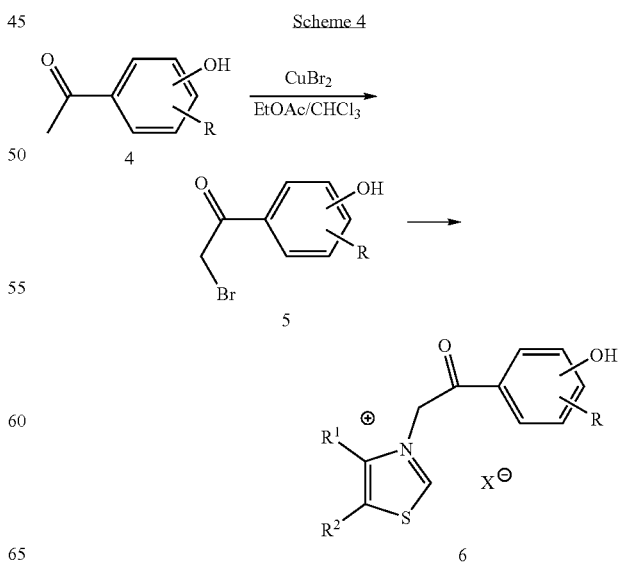

In another synthesis, the preparation of compounds of the formula I wherein R² is —CH₂OH are exemplified. Formamide is first converted to thioformamide by reaction with phosphorus pentasulfide. Thioformamide is reacted with ethyl 2-chloroacetoacetate in dry dioxane as follows:

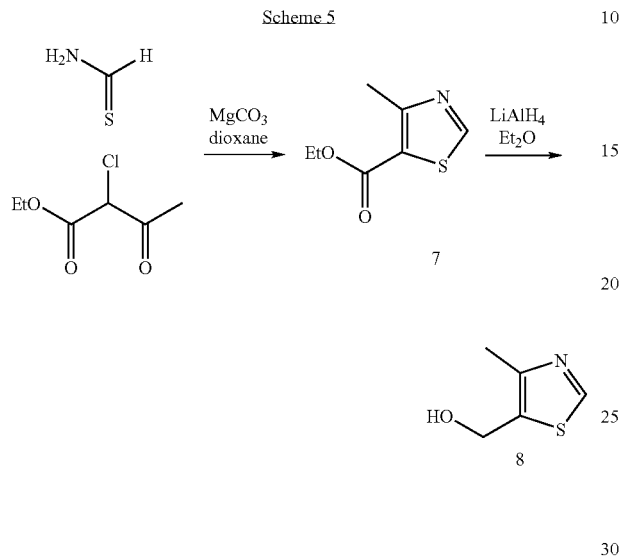

Compound 8 can then be reacted with a suitable alkylating agent to make a compound of the invention.

Where R¹ is —CH₂OH and R² is —CH₃ in Formula I, the route shown in Scheme 6 can be used. The preparation of a thiazole analog containing a 4-hydroxymethyl group, for example, is shown below:

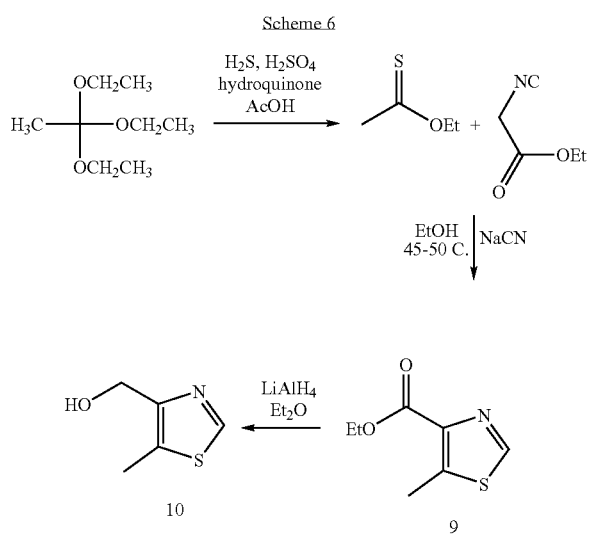

Compound 10 can then be alkylated with a suitable alkylating agent to make a compound of the invention.

Note that reaction conditions indicated in the various reaction schemes are exemplary: such conditions as solvent and temperature are subject to modification within ordinary skill.

A useful synthetic route for the preparation of compounds of formula I wherein Y is —CH(R⁵)CN is shown in Scheme 7.

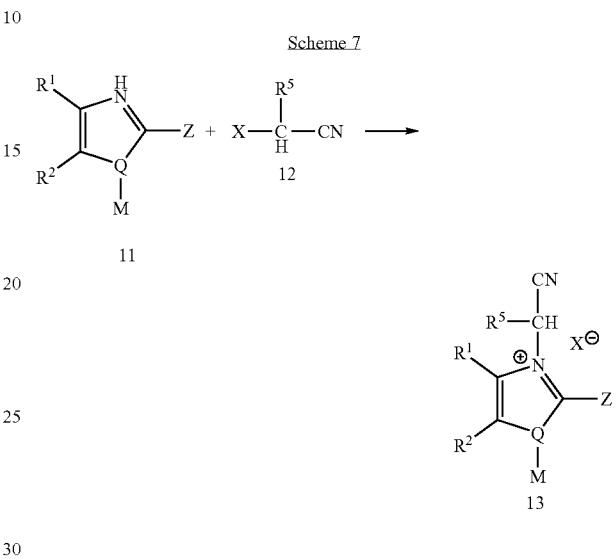

wherein M, Q, R¹, R², R⁵, Y and Z are as described in the text above, and X is a halide, mesitylenesulfonate or other biologically acceptable anion. In Scheme 7, the appropriately substituted imidazole, oxazole, or thiazole of formula 11 is contacted with a (e.g.) halo substituted acetonitrile of formula 12 to produce compounds of the formula 13. The reaction can be performed without any added solvent, or an anhydrous solvent can be utilized as the solvent medium. When a solvent is used, acetonitrile is a typical solvent for this reaction. Reaction times vary according to particular reactants and conditions, but are usually in the range of a few minutes to 48 hours at a temperature of 25-130° C.

Compounds of the formula 17 (below), wherein Y contains a carboxamido moiety, can be synthesized according to method depicted in Scheme 8. An appropriately substituted amine can be condensed with an activated acetyl analog (for example, an acid chloride or acid anhydride), containing an additional leaving group alpha to the carbonyl group, to provide the carboxamide 15. Compound 15 can then be used to alkylate the heterocycle 16 to yield a compound of the invention 17.

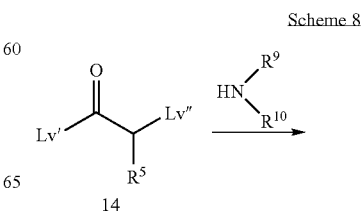

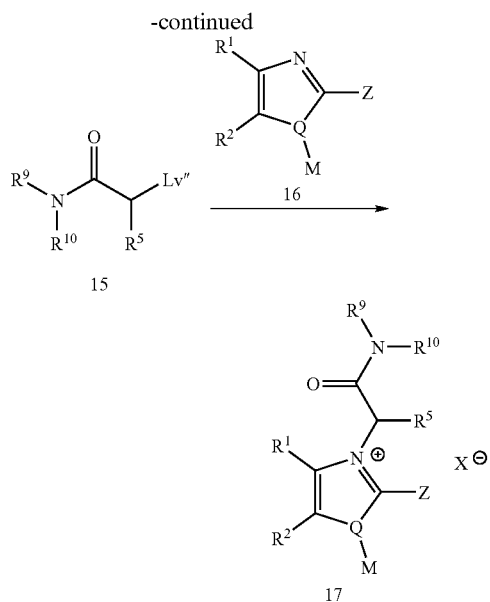

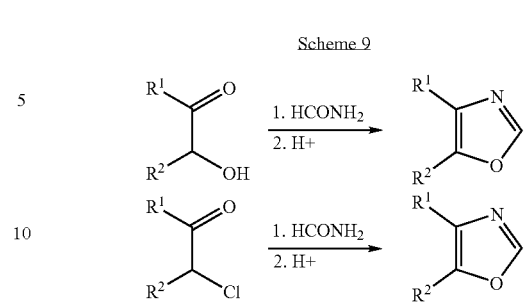

Other alkylation conditions can also be used. For example, thiazoles and imidazoles can be alkylated at the 1-position or the 2-position by vapor phase alkylation over an appropriate solid catalyst, using the corresponding alcohol as the alkyl source. See, Ono et al., in *Catalysis by Microporous Materials*, Studies in Surface Science and Catalysis, Vol. 94, Beyer et al., Eds., 1995, polypeptide.697-704. Appropriate catalysts include zeolite H-Y, zeolite H-ZSM-5 and $H_3PW_{12}O_{40}$ supported on silica. Reaction conditions typically include high temperatures, such as 260 and 300° C.

In addition, N-aryl substituted thiazoliums, oxazoliums and imidazoliums can also be prepared. For example, fluoro phenyl compounds such as 4-fluorobenzoic acid methyl ester can be used to substitute the $N^1$ nitrogen of imidazole to make methyl-4-(1H-imidazol-1-yl)benzoate. See, Morgan et al., *J. Med. Chem.* 33: 1091-1097, 1990. These aryl substituted imidazoliums can then be reacted with an alkylating agent, for example, an α-haloacetophenone analog, to prepare a compound of the invention. Also, the amine functions of imidazoles or amine-substituted thiazoles can be acylated by dehydration or other methods known in the art.

3-Aminothiazoliums, 3-aminooxazoliums, and 1-alkyl-3-aminoimidazoliums can be prepared by reaction with O-mesitylene sulfonylhydroxylamine in methylene chloride. The product mesitylenesulfonate salts can be converted to their chloride salts through ion exchange with strongly basic anion exchange resins.

Substituted oxazole intermediate that are suitable intermediates for the alkylation reactions, such as those shown in Schemes 1 and 7, can be prepared by methods known in the art. For instance, 2-unsubstituted oxazoles can be formed by condensation of formamide with either α-hydroxy or α-haloketones intermediates (H. Bredereck, R. Gommpper, H. G. v. Shuh and G. Theilig, in Newer Methods of Preparative Organic Chemistry, Vol. III, ed. W. Foerst, Academic press, New York, 1964, p. 241). The intermediates can cyclize under acid conditions to form the oxazole ring (Scheme 9). In addition, 2,4-disubstituted oxazoles can be prepared from α-haloketones and amides at higher temperatures using the same method.

Oxazoles can be prepared by cyclization reactions of isonitriles (van Leusen, A. M. *Lect. Heterocycl. Chem.* 1980, 5, S111; Walborsky, H. M.; Periasamy, M. P. in *The Chemistry of Functional Groups, suppl.* C, Patai, S., Rappoport, Z., Eds, Wiley-Interscience, 1983, p. 835; Hoppe, D. *Angew. Chem. Int. Edn. Engl.*, 1974, 13, 789: Schollkopf, U. *Angew. Chem. Int. Ed. Engl.*, 1977, 16, 339). For example, as shown below in Scheme 10, the tosylmetlhyl isocyanide can be deprotonated by a base and reacted with a suitable electrophile (e.g. an aldehyde). The intermediate can cyclize and aromatize to provide the desired oxazole intermediate. The intermediate can then be N-alkylated by the above-described methods to furnish a compound of the invention. Other methods for preparing oxazole intermediates include 1,5-dipolar cyclization of acylated nitrile ylides (Taylor E. C.; Turchi, I. J. *Chem. Rev.*, 1979, 79, 181: Huisgen, R. *Angew. Chem. Int. Edn. Engl.* 1980, 19, 947).

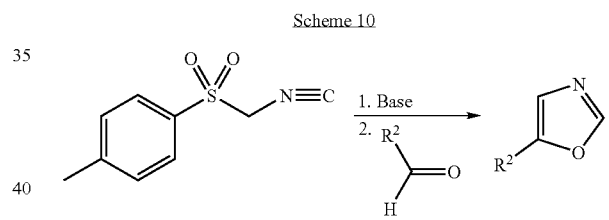

Benzoxazole intermediates substituted at the 2 position can be prepared from 2-aminophenots by acylation with, for example, with an acid chloride and cyclization (Scheme 11). The intermediate can then be N-alkylated by the above-described methods to furnish a compound of the invention.

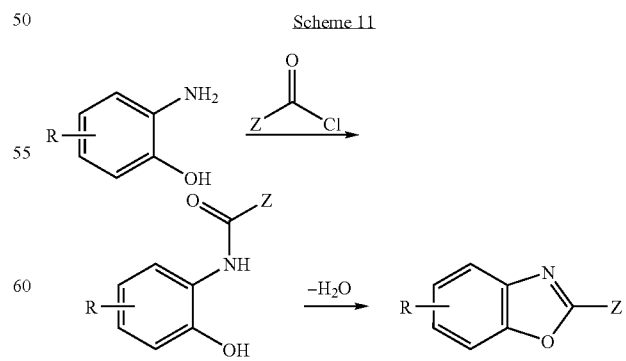

To treat glaucoma or reduced accommodation, and their associated symptoms by administration of an effective amount of a pharmaceutical compound will be recognized by clinicians. The amount includes an amount effective to reduce, ameliorate or eliminate one or more symptoms of the disease sought to be treated or the condition sought to be avoided or treated, or to otherwise produce a clinically recognizable change in the pathology of the disease or condition.

In treating glaucoma, agents of the inventions can be administered concurrently or in a combined formulation with one or more $\alpha_2$-selective adrenergic agonists, carbonic anhydrase inhibitors or prostaglandin analogs. Examples of $\alpha_2$-selective adrenergic agonists include clonidine, apraclonidine, guanfacine, guanabenz and methyldopa, which are administered in effective amounts as is known in the art. Examples of carbonic anhydrase inhibitors include acetazolamide, dichlorphenamide and methazolamide, which are administered in effective amounts as is known in the art. Examples of prostaglandin analogs include $PGE_2$ and $PGF_{2\alpha}$ analogs, which are administered in effective amounts as is known in the art, including effective amounts administered by topical application to the eye. Thus, the invention further provides pharmaceutical compositions comprising an agent of the invention in combination with an effective amount of an $\alpha_2$-selective adrenergic agonist, carbonic anhydrase inhibitor, prostaglandin analog, or combination thereof.

Pharmaceutical compositions can be prepared to allow a therapeutically effective quantity of the compound of the present invention, and can include a pharmaceutically acceptable carrier, selected from known materials utilized for this purpose. See, e.g., Remington, The Science and Practice of Pharmacy, 1995; Handbook of Pharmaceutical Excipients, $3^{rd}$ Edition, 1999. Such compositions can be prepared in a variety of forms, depending on the method of administration, such as sublingual, rectal, nasal, vaginal, topical (including the use of a patch or other transdermal delivery device), by pulmonary route by use of an aerosol, or parenteral, including, for example, intramuscular, subcutaneous, intraperitoneal, intraarterial, intravenous or intrathecal.

In addition to the subject compound, the compositions of this invention can contain a pharmaceutically-acceptable carrier. The term "pharmaceutically-acceptable carrier", as used herein, means one or more compatible solid or liquid filler diluents or encapsulating substances that are suitable for administration to an animal, including a mammal or human. The term "compatible", as used herein, means that the components of the composition are capable of being commingled with the subject compound, and with each other, such that there is no interaction that would substantially reduce the pharmaceutical efficacy of the composition under ordinary use. Preferably when liquid dose forms are used, the compounds of the invention are soluble in the components of the composition. Pharmaceutically-acceptable carriers should, of course, be of sufficiently high purity and sufficiently low toxicity to render them suitable for administration to the animal being treated.

Some examples of substances which can serve as pharmaceutically-acceptable carriers or components thereof are sugars, such as lactose, glucose and sucrose; starches, such as corn starch and-potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the subject compound is basically determined by the way the compound is to be administered. If the subject compound is to be injected, the preferred pharmaceutically-acceptable carrier is sterile, physiological saline, with a blood-compatible suspending agent, the pH of which has been adjusted to about 7.4.

If the preferred mode of administering the subject compound is perorally, the preferred unit dosage form is therefore tablets, capsules, lozenges, chewable tablets, and the like. Such unit dosage forms comprise a safe and effective amount of the subject compound, which is preferably from about 0.7 or 3.5 mg to about 280 mg/70 kg, more preferably from about 0.5 or 10 mg to about 210 mg/70 kg. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder-mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.012% to about 0.933% of the subject compound, more preferably from about 0.033% to about 0.7%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Compositions can also be used to deliver the compound to the site where activity is desired; such as eye drops, gels and creams for ocular disorders.

Compositions of this invention include solutions or emulsions, preferably aqueous solutions or emulsions comprising a safe and effective amount of a subject compound intended for topical intranasal administration. Such compositions preferably comprise from about 0.01% to about 10.0% w/v of a subject compound, more preferably from about 0.1% to about 2.0%. Similar compositions are preferred for systemic delivery of subject compounds by the intranasal route. Compositions intended to deliver the compound systemically by intranasal dosing preferably comprise similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof, and polyvinyl alcohol and acids and bases to adjust the pH of these aqueous compositions as needed. The compositions may also comprise local anesthetics or other actives. These compositions can be used as sprays, mists, drops, and the like.

Other preferred compositions of this invention include aqueous solutions, suspensions, and dry powders comprising a safe and effective amount of a subject compound intended for atomization and inhalation administration. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, including cosolvents as needed to solvate or suspend the active agent; stabilizers such as ascorbic acid, sodium metabisulfite; preservatives such as cetylpyridinium chloride and benzalkonium chloride; tonicity adjustors such as sodium chloride; buffers; and flavoring agents such as sodium saccharin. Such compositions are useful for treating respiratory disorders, such as asthma and the like.

Other preferred compositions of this invention include aqueous solutions comprising a safe and effective amount of a subject compound intended for topical intraocular administration. Such compositions preferably comprise from about 0.01% to about 0.8% w/v of a subject compound, more preferably from about 0.05% to about 0.3%. Such compositions also typically include one or more of preservatives, such as benzalkonium chloride or thimerosal; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases can be used to adjust the pH of these formulations as needed.

Other preferred compositions of this invention useful for peroral administration include solids, such as tablets and capsules, and liquids, such as solutions, suspensions and emulsions (preferably in soft gelatin capsules), comprising a safe and effective amount of a subject compound. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit™ coatings, waxes and shellac.

The compounds of the invention are administered by ocular, oral, parenteral, including, for example, using formulations suitable as eye drops. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. See, Remington's Pharmaceutical Sciences, 16th Ed., Mack Publishing, Easton, Pa., 1980, as well as later editions, for information on pharmaceutical compounding.

Numerous additional administration vehicles will be apparent to those of ordinary skill in the art, including without limitation slow release formulations, liposomal formulations and polymeric matrices.

In another preferred embodiment, the pharmaceutically effective amount is approximately 0.1 or 0.5 to 4 mg/kg body weight daily. Still more preferably, the pharmaceutically effective amount is approximately 1 mg/kg body weight daily. In a preferred embodiment, the amount is administered in once daily doses, each dose being approximately 1 mg/kg body weight.

Compounds of the invention can be used in conjunction with monitoring the improvement (decrease) in the intraocular pressure in a mammal using standard methodology.

The methods of the inventions demonstrate significant utility in animal models that assess ophthalmologic function. For example, a significant improvement in fluid outflow facility was seen in a study of Rhesus monkeys treated using the methods of the invention. FIG. 1 below depicts the results of the experiment in four 16-18-year old Rhesus monkeys that received a single transcorneal injection of 4,5-dimethyl-3-(2-oxo-2-phenylethyl)-thiazolium chloride at a final concentration of 1 mM in the anterior chamber of one eye, and Barany's solution in the adjacent eye. Needle outflow facility measurements were conducted under baseline and pilocarpine-stimulated conditions at 3, 8, 12 and 24 weeks post-administration of 4,5-dimethyl-3-(2-oxo-2-phenylethyl)-thiazolium chloride. The results show a statistically significant increase in baseline outflow facility in the 4,5-dimethyl-3-(2-oxo-2-phenylethyl)-thiazolium chloride treated vs. the control eye at 2 months, and indicate sustained improvement in pilocarpine-stimulated (i.v.) facility at 8-24 weeks. Data from measurement taken during this experiment is presented in Table 1.

TABLE 1

Outflow Facility Data Measured at Increasing Time After Single Intraocular Injection of 4,5-Dimethyl-3-(2-oxo-2-phenylethyl)thiazolium Chloride.

|  | 3 Weeks | | | 8 Weeks | | | 12 Weeks | | |
| --- | --- | --- | --- | --- | --- | --- | --- | --- | --- |
| Baseline | OD | OS | OD/OS | OD | OS | OD/OS | OD | OS | OD/OS |
| 1820 | 0.315 | 0.306 | 1.03 | 0.361 | 0.264 | 1.367 | 0.297 | 0.298 | 0.995 |
| 1821 | 0.233 | 0.215 | 1.082 | 0.34 | 0.244 | 1.395 | 0.271 | 0.436 | 0.623 |

TABLE 1-continued

| | | | | | | | | | |
|---|---|---|---|---|---|---|---|---|---|
| 81051 | 0.365 | 0.369 | 0.989 | 0.648 | 0.462 | 1.403 | 0.508 | 0.365 | 1.393 |
| 81119 | 0.43 | 0.479 | 0.897 | 0.931 | 0.611 | 1.524 | 0.524 | 0.544 | 0.963 |
| Mean | 0.336 | 0.342 | 0.999 | 0.57 | 0.395 | 1.422 | 0.4 | 0.411 | 0.993 |
| SEM | 0.042 | 0.056 | 0.039 | 0.139 | 0.087 | 0.035 | 0.067 | 0.053 | 0.158 |

| | 24 Weeks | | | 9 months | | |
|---|---|---|---|---|---|---|
| Baseline | OD | OS | OD/OS | OD | OS | OD/OS |
| 1820 | | | | 0.749 | 0.492 | 1.524 |
| 1821 | 0.271 | 0.436 | 0.623 | 0.195 | 0.064 | 3.053 |
| 81051 | 0.354 | 0.469 | 0.753 | | | |
| 81119 | 0.605 | 0.579 | 1.046 | | | |
| Mean | 0.41 | 0.495 | 0.907 | 0.472 | 0.276 | 2.239 |
| SEM | 0.1 | 0.043 | 0.126 | 0.277 | 0.214 | 0.765 |

| Post Rx#1--Pilo 1 mg/kg of 0.2% IV | | | | | | | | | |
|---|---|---|---|---|---|---|---|---|---|
| | 3 Weeks | | | 8 Weeks | | | 12 Weeks | | |
| | OD | OS | OD/OS | OD | OS | OD/OS | OD | OS | OD/OS |
| 1820 | 0.661 | 0.53 | 1.248 | 0.696 | 0.379 | 1.837 | 1.001 | 0.443 | 2.263 |
| 1821 | 0.623 | 0.297 | 2.097 | 0.649 | 0.224 | 3.794 | 0.632 | 0.673 | 0.938 |
| 81051 | 3.369 | 3.842 | 0.877 | 1.69 | 1.675 | 1.009 | 2.081 | 0.772 | 2.698 |
| 81119 | 8.981 | 4.965 | 1.809 | 5.215 | 3.427 | 1.522 | 1.957 | 3.087 | 0.634 |
| Mean | 3.409 | 2.408 | 1.508 | 2.113 | 1.426 | 2.04 | 1.418 | 1.244 | 1.865 |
| SEM | 1.966 | 1.175 | 0.274 | 1.057 | 0.742 | 0.609 | 0.356 | 0.618 | 0.626 |

| Post Rx#1--Pilo 1 mg/kg of 0.2% IV | | | | | | |
|---|---|---|---|---|---|---|
| | 24 Weeks | | | 9 months | | |
| | OD | OS | OD/OS | OD | OS | OD/OS |
| 1820 | | | | 0.561 | 0.55 | 1.047 |
| 1821 | 0.532 | 0.673 | 0.938 | 0.41 | 0.059 | 5.966 |
| 81051 | 0.873 | 0.596 | 1.464 | | | |
| 81119 | 3.364 | 2.387 | 1.409 | | | |
| Mean | 1.623 | 1.219 | 1.27 | 0.545 | 0.355 | 4.007 |
| SEM | 0.973 | 0.565 | 0.167 | 0.135 | 0.296 | 2.96 |

| Post Rx#1/Baseline | | | | | | | | | |
|---|---|---|---|---|---|---|---|---|---|
| | 3 Weeks | | | 8 Weeks | | | 12 Weeks | | |
| | OD | OS | OD/OS | OD | OS | OD/OS | OD | OS | OD/OS |
| 1820 | 2.1 | 1.733 | 1.212 | 1.926 | 1.433 | 1.344 | 3.375 | 1.483 | 2.275 |
| 1821 | 2.678 | 1.381 | 1.938 | 2.497 | 0.918 | 2.72 | 2.327 | 1.545 | 1.507 |
| 81051 | 9.226 | 10.404 | 0.887 | 2.61 | 3.629 | 0.719 | 4.098 | 2.117 | 1.936 |
| 81119 | 20.905 | 10.365 | 2.017 | 5.602 | 5.609 | 0.999 | 3.736 | 5.674 | 0.658 |
| Mean | 8.727 | 5.971 | 1.514 | 3.159 | 2.697 | 1.446 | 3.384 | 2.705 | 1.594 |
| SEM | 4.369 | 2.549 | 0.277 | 0.826 | 1.078 | 0.444 | 0.382 | 1 | 0.349 |

| Post Rx#1/Baseline | | | | | | |
|---|---|---|---|---|---|---|
| | 24 Weeks | | | 9 months | | |
| | OD | OS | OD/OS | OD | OS | OD/OS |
| 1820 | | | | 0.903 | 1.322 | 0.567 |
| 1821 | 2.327 | 1.545 | 1.507 | 2.095 | 0.916 | 2.262 |
| 81051 | 2.469 | 1.27 | 2.526 | | | |
| 81119 | 5.561 | 4.126 | 1.111 | | | |
| Mean | 3.462 | 2.314 | 1.716 | 1.502 | 1.121 | 1.468 |
| SEM | 1.065 | 0.91 | 0.422 | 0.594 | 0.202 | 0.795 |

| Post Rx#2--Pilo 100 µg/µl I.C. | | | | | | | | | |
|---|---|---|---|---|---|---|---|---|---|
| | 3 Weeks | | | 8 Weeks | | | 12 Weeks | | |
| | OD | OS | OD/OS | OD | OS | OD/OS | OD | OS | OD/OS |
| 1820 | 1.774 | 1.793 | 0.99 | 1.094 | 1.672 | 0.0655 | 1.796 | 0.883 | 2.033 |
| 1821 | 1.355 | 0.522 | 2.596 | 0.867 | 0.315 | 2.753 | 1.457 | 0.63 | 2.315 |
| 81051 | 5.529 | 3.843 | 1.439 | 4.539 | 3.241 | 1.401 | 4.47 | 1.226 | 3.646 |
| 81119 | 13.03 | 5.879 | 2.216 | 14.385 | 6.823 | 2.108 | 3.374 | 3.237 | 1.042 |
| Mean | 5.422 | 3.009 | 1.81 | 5.221 | 3.013 | 1.729 | 2.744 | 1.494 | 2.259 |

TABLE 1-continued

| | | | | | | | | |
|---|---|---|---|---|---|---|---|---|
| SEM | 2.704 | 1.176 | 0.364 | 3.168 | 1.404 | 0.425 | 0.703 | 0.594 | 0.537 |

| | Post Rx#2--Pilo 100 µg/µl I.C. | | | | | |
|---|---|---|---|---|---|---|
| | 24 Weeks | | | 9 months | | |
| | OD | OS | OD/OS | OD | OS | OD/OS |
| 1820 | | | | 1.805 | 1.418 | 1.273 |
| 1821 | 1.457 | 0.63 | 2.315 | 1.111 | 0.043 | 25.706 |
| 81051 | 1.516 | 0.6 | 2.526 | | | |
| 81119 | 4.318 | 3.942 | 1.111 | | | |
| Mean | 2.461 | 1.724 | 1.984 | 1.435 | 0.731 | 13.491 |
| SEM | 0.965 | 1.109 | 0.441 | 0.347 | 0.683 | 12.21 |

Figure 2:
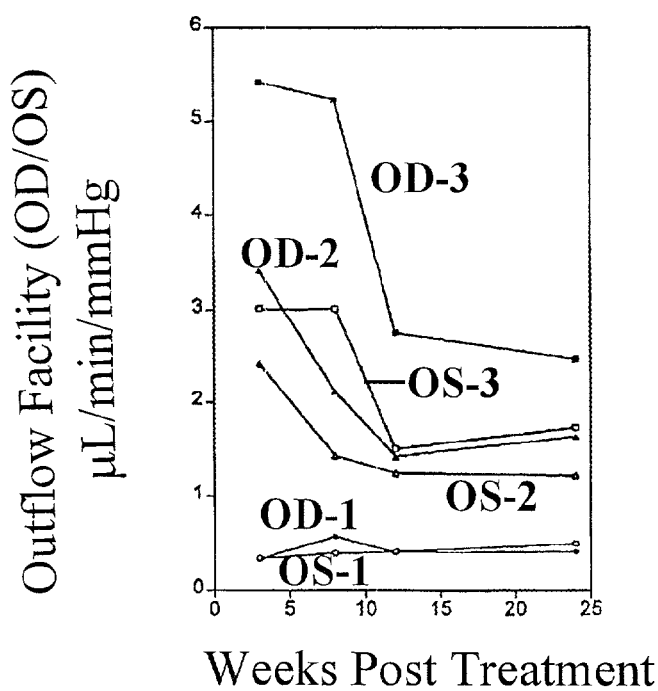
FIG. 2 depicts the effect of pilocarpine route of administration on outflow facility post treatment with 4,5-dimethyl-3-(2-oxo-2-phenylethyl)-thiazolium chloride.

The enhancement of outflow facility by pilocarpine following a single 4,5-dimethyl-3-(2-oxo-2-phenylethyl)-thiazolium chloride treatment is influenced by the route of administration of the cholinergic agonist as shown in FIG. 2. Shown are control values for baseline (OS-1), i.v. stimulation with pilocarpine (0.2%, 1 mL/kg) (OS-2), and intracameral stimulation with pilocarpine (100 µg/10 µL) (OS-3). Also shown are the corresponding experimental values (OD-1, OD-2, OD-3). Administration of the cholinergic agent, pilocarpine intravenously (i.v.) produces an enhancement over that of baseline while direct administration to the intraocular fluid by the intracameral route (i.c.) magnifies this cholinergic response. These results highlight the role of muscular innervation in the control of the intraocular fluid filtering mechanism and would seem to indicate that some physical movement of the trabecular meshwork is necessary to permit passage of intraocular fluid. Enhancement of this passage of fluid following 4,5-dimethyl-3-(2-oxo-2-phenylethyl)-thiazolium chloride treatment indicates that AGE cross-links that have previously formed between the proteins of the trabecular meshwork have a role in causing the resistance to fluid flow.

As is apparent, the cholinergic-stimulated outflow was greatly increased over that of the non-stimulated outflow and indicates that following treatment with 4,5-dimethyl-3-(2-oxo-2-phenylethyl)-thiazolium chloride a greater responsiveness of the trabecular meshwork to nervous input was achieved. The results described in the above experiment demonstrate improvement in ophthalmologic function.

In addition to the increased fluid outflow facility, the methods of the invention provide improvement in pilocarpine-stimulated accommodation (i.e., the process of effecting refractive changes in the shape of the lens) in animal studies. As in the regulation of outflow facility, cholinergic input stimulates the movement of the ciliary muscle to control the shape of the lens, and allows accommodation in conditions of low illumination. Accommodation is impaired in a vast majority of individuals and begins to become noticeable to the individual around the age of 40 years. Interestingly, changes in accommodative response occur much earlier in life, around 18 years of age, and progress until vision is noticeably impaired.

Figure 4:
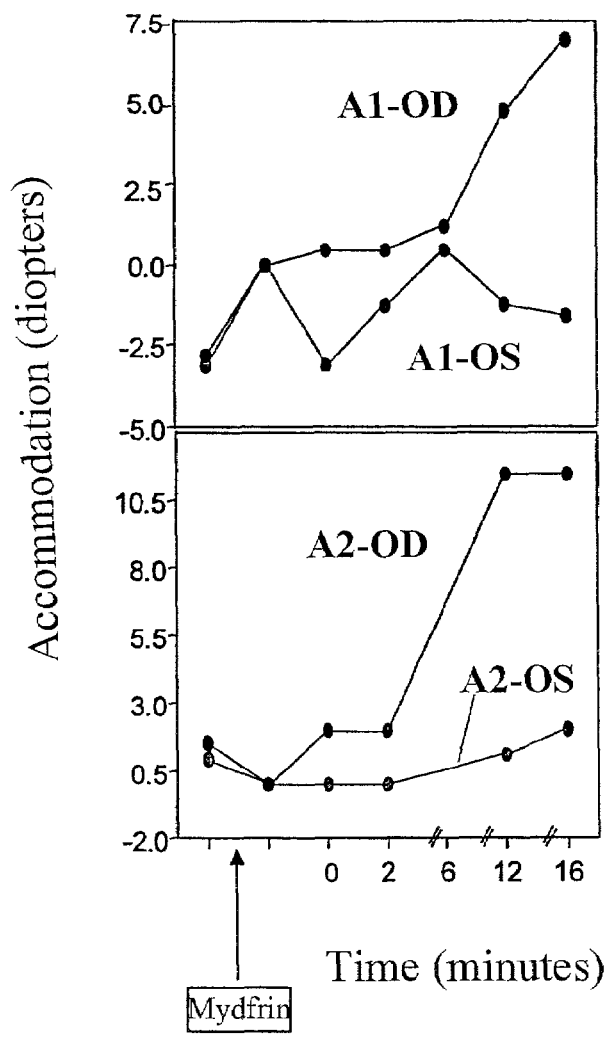
FIG. 4 depicts the effect of 4,5-dimethyl-3-(2-oxo-2-phenylethyl)-thiazolium chloride on intramuscular pilocarpine-stimulated accommodative response in primates.

Physiological studies on accommodation in primates (Rhesus monkeys) were conducted following intraocular injection of 4,5-dimethyl-3-(2-oxo-2-phenylethyl)-thiazolium chloride (at a final concentration of 1 mM). Animals were treated for four day, twice a day (once a day on weekends) with 2 µg PGF2α followed 2 hours later with and an intraocular injection of 10 µL of 4,5-dimethyl-3-(2-oxo-2-phenylethyl)-thiazolium chloride at a final concentration of 1 mM in the eye. The needle was kept in the eye for 30 minutes post injection. No injection was made to the control eye. 24 hours after the last injection of 4,5-dimethyl-3-(2-oxo-2-phenylethyl)-thiazolium chloride, a course of therapy consisting of once a day dosing for a total of 4 days, accommodative responses to i.m. pilocarpine administration was performed following phenylephrine refraction (Mydfrin™, for dilating the pupils). The results in FIG. 4 are for two animals with control (OS) and experimental (OD), and indicated an improvement in pilocarpine-stimulated accommodation in the animals that were studied.

Figure 3:
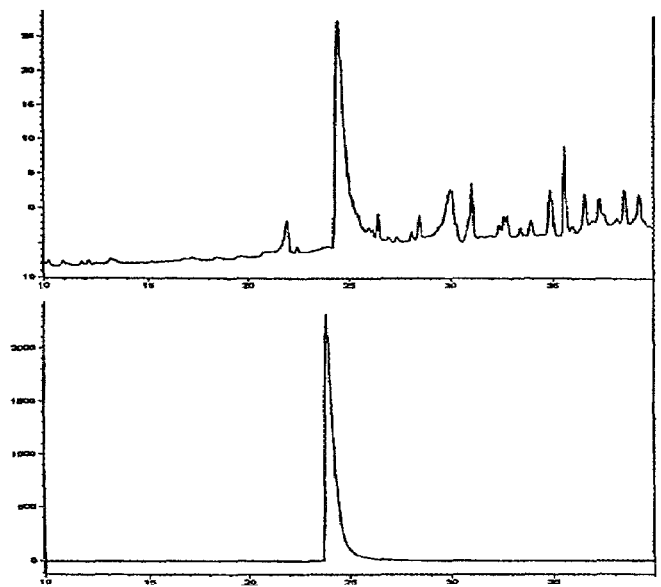
FIG. 3 depicts the penetration of 4,5-dimethyl-3-(2-oxo-2-phenylethyl)-thiazolium chloride through an intact rabbit cornea.

Compounds of the invention are able to gain access to the anterior chamber of the eye following topical administration of eye drops. For example, 4,5-dimethyl-3-(2-oxo-2-phenylethyl)-thiazolium chloride was tested in vitro through an intact rabbit cornea for transcorneal penetration in a standard diffusion chamber apparatus (FIG. 3). Corneas were mounted in a chamber in vitro at 37° C. with the epithelial side exposed to 4,5-dimethyl-3-(2-oxo-2-phenylethyl)-thiazolium chloride in Barany's Solution. 1 ml samples were taken from the endothelial side 1 hour after addition of 4,5-dimethyl-3-(2-oxo-2-phenylethyl)-thiazolium chloride at a final concentration of 1 mM to the epithelial chamber. The volume of the chamber was replaced with phosphate buffered saline. The chromatogram shown above is from a 1 hour time point, with penetration calculated at 0.5%. The 1 ml sample was injected onto a 2 ml sample loop in an BPLC gradient system with a Medichem Inertsil ODS2, 5 micron column of dimensions 4.6×250 mm in 0.05 M sodium phosphate buffer, pH 7.4 with 10% acetonitrile. The gradient was from 10%-40% acetonitrile over 30 min. The top panel shows a penetration study, which can be compared to the control elution of the bottom panel. A penetration value of 0.5%-1.0% was observed at 1 and at 5 hours of diffusion, respectively.

The success of corneal penetration of compounds of the invention was further demonstrated in vivo in Cynomolgus monkeys. A penetration study was conducted in the eyes of presbyotic monkeys using experimental procedures similar to those cited above. During these studies, penetration of 4,5-dimethyl-3-(2-oxo-2-phenylethyl)-thiazolium chloride was evaluated with an eye-cup which held a solution of 10 mM 4,5-dimethyl-3-(2-oxo-2-phenylethyl)-thiazolium chloride in Barany's solution for 5 hours. A sample of 4,5-dimethyl-3-(2-oxo-2-phenylethyl)-thiazolium chloride was recovered from the anterior chamber and the quantity of remaining compound analyzed with EPLC. Results indicate that approximately 2-4% of 4,5-dimethyl-3-(2-oxo-2-phenylethyl)-thiazolium chloride was recoverable in the anterior chamber of the eye following a 5 hour exposure to topical administration of the compound.

The activity of the compounds of the invention in breaking, reversing or inhibiting the formation of AGE's or AGE-mediated crosslinks can be assayed by any of the methods described in U.S. Pat. No. 5,853,703.

The following examples further illustrate the present invention, but of course, should not be construed as in any way limiting its scope.

EXAMPLE 1

3-(2-Phenyl-2-hydroxyethyl)-4,5-dimethylthiazolium chloride: 2-Chloro-1-phenylethanol 2-Chloroacetophenone (5.0 g, 32 mmol) was dissolved in methanol (25 mL) and cooled to 0° C. Sodium borohydride (1.2 g, 32 mmol) was added and stirred at 0° C. for 30 minutes. The reaction mixture was neutralized by adding conc. HCl to pH 7.0 and evaporated to dryness. The residue was dissolved in ethanol (30 mL) and filtered, washed with ethanol. The ethanol was evaporated to dryness. The residue was dissolved in methylene chloride (20 mL) and dried over sodium sulfate. The methylene chloride solution was filtered and evaporated to give the desired product as an oil; yield 4.84 g (5.6%).

3-(2-Phenyl-2-hydroxyethyl)-4,5-dimethylthiazolium chloride.

The neat mixture of 2-chloro-1-phenylethanol (2.34 g, 14.9 mmol) and 4,5-dimethylthiazole (1.69 g, 14.9 mmol) were heated with stirring at 135° C. for 28 hrs. It was cooled to room temperature and water (30 mL) was added to the reaction mixture with stirring, and then was extracted with ether (30 mL). The water layer was treated with actived carbon and evaporated to dryness. It was crystallized from a mixture of acetonitrile and ether to give a racemic product as prisms; 0.39 g (9.7%); mp. 201-203° C.

EXAMPLE 2

S3-(2-Phenyl-2-hydroxyethyl)-4,5-dimethylthiazolium chloride

S(−)2-chloro-1-phenylethanol

2-Chloroacetophenone (3 g., 19.4 mmol) was treated with (−) DIP-chloride (6.7 g., 20.9 mmol) in anhydrous THF (20 mL) at dry-ice bath temperature and left overnight. The temperature was raised to room temperature and THF was removed in vacuo. The residue was dissolved in ether (100 mL). The diethanolamine (4.58 g., 42.6 mmol) was added and the mixture stirred at room temperature for 5 hrs. The separated solid was filtered and the filtered cake was washed with hexane (40 mL) and ether (30 mL). The combined filtrates were evaporated to dryness to give 6.36 g of crude product. This was purified by silica gel column chromatography using 1% ether and petroleum ether 1.71 g (56%) of the desired product was obtained as an oil.

S3-(2-Phenyl-2-hydroxyethyl)-4,5-dimethylthiazolium chloride

The neat mixture of S(−)2-chloro-1-phenylethanol (2.78 g., 17.8 mmol) and 4,5-dimethylthiazole (2 g., 17.7 mmol) were heated with stirring at 135° C. for 25 hrs. It was cooled to room temperature and water (30 mL) was added to the reaction mixture with stirring. The solution was extracted with ether (30 mL). The ether extract was again extracted with water (30 mL). The combined water layer was evaporated to dryness and the residue was crystallized with a mixture of acetonitrile and methyl tert-butyl ether. Yield: 0.63 g. (7.7%); mp. 189-190° C.; $[\alpha]_D^{25}$ −51.765 (Water, c=1.7732).

EXAMPLE 3

R(+)3-(2-Phenyl-2-hydroxyethyl)-4,5-dimethylthiazolium chloride

R(+) 2-chloro-1-phenylethanol

2-Chloroacetophenone (6.25 g., 40.4 mmol) was treated with (+) DIP-chloride (18 g., 56.1 mmol) in anhydrous THF (40 mL) at dry-ice bath temperature and left overnight. The temperature was raised to room temperature and THF was removed in vacuo. The residue was dissolved in ether (210 mL). The diethanolamine (9 g., 8 5.6 mmol) was added and the mixture stirred at room temperature for 5 hrs. The separated solid was filtered and the filtered cake was washed with ether (150 mL). The combined filtrates were evaporated to dryness to give 15.53 g. of crude product. This was purified by silica gel column chromatography using 1% ether and petroleum ether 4.32 g (68%) of the desired product as an oil.

R(+)3-(2-Phenyl-2-hydroxyethyl)-4,5-dimethylthiazolium chloride

The neat mixture of R(+)2-chloro-1-phenylethanol (4.32 g., 27.6 mmol) and 4,5-dimethylthiazole (3.12 g, 27.6 mmol) were heated with stirring at 135° C. for 25 hrs. It was cooled to room temperature and water (30 mL) was added to the reaction mixture with stirring. The solution was extracted with ether (30 mL). The ether extract was again extracted with water (30 mL). The combined water layer was evaporated to dryness and the residue was crystallized with a mixture of acetonitrile and methyl tert-butyl ether. Yield: 0.44 g. (5.4%); mp. 187-189° C.; $[\alpha]_D^{25}$ +52.009 (Water, c=1.782).

EXAMPLE 4

3-[2-(2', 3' or 4'-monohydroxyphenyl)-2-oxoethyl]-4,5-dimethylthiazolium bromide 2-Bromo-4'-hydroxyacetophenone Copper (II) bromide (6 g, 26.9 mmol) was suspended in ethyl acetate (50 mL) and 4'-hydroxyacetophenone (2 g, 14.7 mmol) dissolved in chloroform (20 mL) was added to the suspension. The reaction mixture was refluxed for 8 hrs. and filtered hot through celite pad. The filtrate was evaporated to dryness to give the desired crude brown colored compound (mp=115-118° C.; yield: 3.03 g, 96%). The NMR spectrum and TLC [silica gel, Hexanes:EtOAc (1:1, v/v)] was in agreement with the desired product. It was used as such in the next step of the reaction without further purification.

This method was used to prepare:
(i) 2-Bromo-2'-hydroxyacetophenone from 2'-hydroxyacetophenone and copper (II) bromide. Yield: 3.30 g. (95%; oil).
(ii) 2-Bromo-3'-hydroxyacetophenone from 3'-hydroxyacetophenone and copper (II) bromide. Yield: 3.20 g. (92%; oil).

3-[2-(4-Hydroxyphenyl)-2-oxoethyl]-4,5-dimethylthiazolium bromide

The neat mixture of 2-bromo-4'-hydroxyacetophenone (3 g, 15 mmol) and 4,5-dimethylthiazole (1.71 g, 15 mmol) was heated at 110° C. for 3 hrs. It was dissolved in acetonitrile (15 mL) and cooled to room temperature. Tert-butyl methyl ether (5 mL) was added and the reaction mixture kept at room temperature overnight. The product crystallized was filtered, washed well with a mixture of acetonitrile and tert-butyl methyl ether (1:1, v/v) and dried. It was recrystallized from a mixture of acetonitrile, ethyl alcohol and tert-butyl methyl ether. Yield: 3.18 g (64%); mp. 245-247° C. (dec.).

This method was used to prepare:
(i) 3-[2-(2-Hydroxyphenyl)-2-oxoethyl]-4,5-dimethylthiazolium bromide from 2-bromo-2'-hydroxyacetophenone and 4,5-dimethylthiazole. Yield: 2.05 g. (38%), mp=208-209° C.
(ii) 3-[2-(3-Hydroxyphenyl)-2-oxoethyl]-4,5-dimethylthiazolium bromide from 2-bromo-3'-hydroxyacetophenone and 4,5-dimethylthiazole. Yield: 1.52 g. (47%), mp=235-237° C.

EXAMPLE 5

3-(2-Phenyl-2-oxoethyl)-4-methyl-5-(hydroxymethyl)thiazolium chloride

Thioformamide

To formamide (20 g, 443 mmol) dissolved in anhydrous THF (100 mL) was added phosphorous pentasulfide ($P_2S_5$) (20 g, 45 mmol) while maintaining the temperature at 30-35° C. The mixture was stirred overnight at room temperature, filtered and stripped of THF. The crude product was suspended in ethyl acetate (40 mL) and cooled at −78° C. overnight, filtered and dried in vacuo at room temperature to give thioformamide (10.6 g, 39%). See Rynbrandt, R. H., Nishizawa, E. E., Balogoyen, D. P., Mezdoza, A. K., Annis, K. A.; *J. Med. Chem.* 1981, 24, 1507-1510.

4-Methyl-5-(ethoxycarbonyl)thiazole

Thioformamide (7.5 g, 122.72 mmol), ethyl 2-chloroacetoacetate (16.4 g, 99.52 mmol) and magnesium carbonate (20 g, 237.22 mmoL) were taken dioxane (100 mL) and heated at 110° C. for 4 hrs. The reaction mixture was cooled to room temperature and filtered to remove magnesium carbonate. The solvent was evaporated to dryness and the residue was taken in ether (200 mL) and washed successively with 0.5 M NaOH solution (200 mL×2) and saturated brine solution (100 mL) and dried over $Na_2SO_4$. It was filtered and evaporated to give 4-methyl-5-(ethoxycarbonyl)thiazole as an oil which was purified by silica gel column chromatography using hexanes:EtOAc (8:2, v/v) as a eluent; yield: 3.28 g (17%).

4-Methyl-5-(hydroxymethyl)thiazole

A 250-mL, three necked round-bottomed flask fitted with a 100-mL dropping funnel, a nitrogen-inlet tube, and a reflux condenser was added lithium aluminum hydride (1 g, 26.35 mmol) and anhydrous ether (50 mL). To the dropping funnel was added 4-methyl-5-(ethoxycarbonyl)-thiazole (3 g, 17.3 mmol) and anhydrous ether (25 mL). While the suspension of lithium aluminum hydride was gently stirred under a nitrogen atmosphere, the solution of 4-methyl-5-(ethoxycarbonyl) thiazole was added dropwise at a rate maintaining a gentle reflux. When the addition was complete, the mixture was heated at reflux for 4 hrs. After the mixture had returned to room temperature, anhydrous ether (100 mL) was added. The gray reaction mixture was hydrolyzed by addition, in small parts, of a sufficient amount of wet sodium sulfate. The reaction mixture was filtered through a sintered-glass funnel. The organic layer separated and dried over $Na_2SO_4$. It was filtered and evaporated to give desired compound as an oil; yield: 590 mg (26%).

3-(2-Phenyl-2-oxoethyl)-4-methyl-5-(hydroxymethyl)thiazolium chloride.

The neat reaction of 4-methyl-5-(hydroxymethyl)thiazole (590 mg, 4.57 mmol) and 2-chloroacetophenone (710 mg, 4.59 mmol) was heated at 110° C. The mixture solidified within 15 minutes. Acetonitrile (10 mL) was added and the mixture refluxed for another 3 hrs. It was cooled to room temperature and tert-butyl methyl ether (5 mL) was added and the reaction mixture was left overnight at room temperature. The product crystallized was filtered and washed well with a mixture of hexanes: EtOAc (1:1, v/v) and dried. It was recrystallized from a mixture of acetonitrile/ethanol/ tert-butyl methyl ether; yield 130 mg (10%); mp.240-242° C. (dec.).

EXAMPLE 6

3-[2-(Disubstituted-dihydrooxyphenyl)-2-oxoethyl]-4,5-dimethylthiazolium bromide 2-Bromo-2',4'-dihydroxyacetophenone.

Copper (II) bromide (6 g, 26.9 mmol) was suspended in ethyl acetate (50 mL) and 2',4'-dihydroxyacetophenone (2 g, 13.1 mmol) dissolved in chloroform (20 mL) was added to the suspension. The reaction mixture was refluxed for 8 hrs. and filtered hot through celite pad. The filtrate was evaporated to dryness to give crude oil (3.0 g, 96%). The NMR spectrum and TLC [silica gel, Hexanes:EtOAc (1:1, v/v)] was in agreement with the desired product. It was used as such in the next step of the reaction without further purification.

This method was used to prepare:
(i) 2-Bromo-3',5'-dihydroxyacetophenone from 3',5'-dihydroxyacetophenone and copper (II) bromide.
(ii) 2-Bromo-2',5'-dihydroxyacetophenone from 2',5'-dihydroxyacetophenone and copper (II) bromide. Yield: 2.99 g; 99%

3-[2-(2,4-Dihydroxyphenyl)-2-oxoethyl]-4,5-dimethylthiazolium bromide

The neat mixture of 2-bromo-2',4'-dihydroxyacetophenone (3 g, 13 mmol) and 4,5-dimethylthiazole (1.71 g, 13.3 mmol) was heated at 110° C. for 3 hrs. It was dissolved in acetonitrile (15 mL) and cooled to room temperature. Tert-butyl methyl ether (5 mL) was added and the reaction mixture kept at room temperature overnight. The product crystallized was filtered, washed well with a mixture of acetonitrile and tert-butyl methyl ether (1:1, v/v) and dried. It was recrystallized from a mixture of methanol and a few drops of water. Yield: 2.5 g (50%); mp. 257-260° C. (dec.).

This method was used to prepare: (
i) 3-[2-(3,5-Dihydroxyphenyl)-2-oxoethyl]-4,5-dimethylthiazolium bromide in 55% yield from 2-bromo-3',5'-dihydroxyacetophenone and 4,5-dimethylthiazole; mp. 257-258° C. Yield: 2.05 g (21%).
(ii) 3-[2-(2,5-Dihydroxyphenyl)-2-oxoethyl]-4,5-dimethylthiazolium bromide in 57% yield from 2-bromo-2,5-dihydroxyacetophenone and 4,5-dimethylthiazole; mp.231-232° C. Yield: 4.03 g (52%).
(iii) 3-[2-(3,4-Dihydroxyphenyl)-2-oxoethyl]-4,5-dimethylthiazolium chloride in 60% yield from commercially available 2-chloro-3',4'-dihydroxyacetophenone and 4,5-dimethylthiazole; mp. 260-263° C. (dec.); yield: 3.9 g (48%).

EXAMPLE 7

Preparation of
1-methyl-3-(cyanomethyl)imidazolium bromide

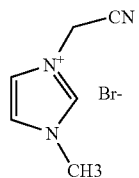

A mixture of 1-methylimidazole (1 g, 12.2 mmol) and bromoacetonitrile (1.46 g, 12.2 mmol) were combined and stirred. An exothermic reaction was produced and the product precipitated from the reaction mixture. After cooling the reaction mixture is allowed to cool to room temperature acetonitrile ($CH_3CN$) (2 mL) is added. The crude product is recovered by filtration and washed with additional $CH_3CN$. The crude product is dissolved in $H_2O$, treated with decolorizing carbon and evaporated in vacuo to dryness. The product is further purified by recrystallization from a mixture of ethanol EtOH, $CH_3CN$ and diethyl ether to yield 1-methyl-3-(2-cyanomethylene)-imidazolium bromide as a white crystalline solid: mp 165-167° C.

EXAMPLE 8

Preparation of
3-(cyanomethyl)-4,5-dimethylthiazolium bromide

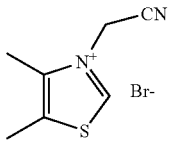

A mixture of 4,5-dimethylthiazole and bromoacetonitrile were heated with stirring at 95° C. for 1 hour. The product precipitated from the mixture within 30 minutes. After cooling to room temperature, the product a solution of 30% v/v of diethyl ether: $CH_3CN$ (10 mL) was added with stirring. The crude product was recovered by filtration, and recrystallized from a mixture of EtOH and $CH_3CN$ to yield 2.136 g of 3-(cyanomethyl)-4,5-dimethylthiazolium bromide as needles: mp 184-186° C. (dec.).

EXAMPLE 9

Preparation of
3-(cyanomethyl)-4,5-cyclohexenothiazolium
bromide

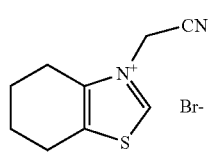

A mixture of thioformamide (0.8 g), 2-chlorocyclohexan-1-one (1.73 g), $MgCO_3$ (1.5 g) was refluxed in dioxane (12 mL) for 30 h. The reaction mixture was evaporated in vacuo, and the concentrated poured into diethyl ether (30 mL). The resulting ethereal solution was washed with 1% NaOH solution (3×15 mL). The combined NaOH solution was back extracted with diethyl ether. The ether layers were combined, washed with saturated NaCl soution until neutral, and then dried over $Na_2SO_4$. The ethereal solution was evaporated in vacuo to afford 1.02 g of 4,5-cyclohexenothiazole.

A mixture of 4,5-cyclohexenothiazole (1 g, 7.2 mmol) and bromoacetonitrile (0.863 g, 7.2 mmol) were heated at 120° C. for 1 h. After cooling the reaction mixture was treated with a solution of 30% diethyl ether in $CH_3CN$ (10 mL). The product was recovered by filtration and washed with additional 30% diethyl ether in $CH_3CN$. The product was recrystallized from a mixture of EtOH and $CH_3CN$ to yield 0.752 g of 3-(cyanomethyl)-4,5-cyclohexenothiazolium bromide as a crystalline solid: mp 215-217° C. (dec.).

The preparation of 3-(2-cyanomethyl)-4,5-cyclopentenothiazolium bromide from 2-chlorocyclopentan-1-one is conducted as in the above procedure.

EXAMPLE 10

Preparation of 3-[2-(1-pyrrolidinyl)-2-oxoethyl]-1,2-dimethylimidazolium chloride N-(chloroacetyl)pyrrolidine Pyrrolidine (63.9 g, 0.9 mole) was taken up in $CH_2Cl_2$ (640 mL) and cooled to 0° C. in a salt-ice water bath. To the stirred mixture was added chloroacetyl chloride (101.8 g in 450 mL of $CH_2Cl_2$, 0.9 mole) dropwise maintaining the internal temperature below 15° C. After adding the chloroacetyl chloride, the mixture was stirred for one hour at 5° C. Sodium hydroxide solution (7 M, 190 mL) was added with vigorous stirring such that the inside temperature did not exceed 20° C. The mixture was stirred for 15 minutes and the aqueous layer was separated. The organic layer was washed with saturated sodium bicarbonate solution (2×200 mL), water (1×200 mL) and dried over anhydrous sodium sulfate. The solvent was removed in vacuo and the residue was recrystallized from hexane to give 64.5 g (48.6% yield) of white plate crystals; mp 43° C.

3-[2-(1-pyrrolidinyl)-2-oxoethyl]-1,2-dimethylimidazolium chloride

A mixture of N-(chloroacetyl)pyrrolidine (2.0 g, 13.55 mmol) and 1,2-dimethylimidazole (1.3 g, 13.5 mmol) were heated neat at 110° C. for 3 hours. To the reaction mixture was added acetonitrile (5 mL), and heating was continued for 20 minutes. Tert-butyl methylether (10 mL) was added, and the resulting mixture was allowed to stand at room temperature overnight. The product was recovered by filtration, and washed with a mixture of tert-butyl methyl ether and acetonitrile (7:3 v/v, 50 mL). The crude product was recrystallized from a mixture of acetonitrile and tert-butyl methyl ether to obtain 1.23 g (41%) of a white solid; mp 191-193° C.

EXAMPLE 11

Preparation of 1-butyl-3-aminoimidazolium
mesitylene sulfonate

An ice-cold solution of 1-butylimidazole (7.0 g, 16.30 mmol) in anhydrous $CH_2Cl_2$ (35 mL) was treated dropwise with a solution of O-mesitylene sulfonylhydroxylamine (17.8 g, 16.50 mmol) in $CH_2Cl_2$ (70 mL). After stirring for 6 hours in the ice-bath, ether (210 mL) was added with stirring over the course of 1 hour. The resulting mixture was allowed to stand at −16° C. overnight. The product was recovered by filtration, and washed with a mixture of $CH_2Cl_2$: ether (3:1 v/v) to yield a white amorphous powder; 16.70 g. The crude product was recrystallized from a mixture of $CH_2Cl_2$ (80 mL) and ether (80 mL) to give 12.40 g; mp 71-73° C.

EXAMPLE 12

Effect of
4,5-Dimethyl-3-(2-oxo-2-phenylethyl)thiazolium
chloride on Outflow Facility in Primates Four 16-18 year old rhesus monkeys received a single transcorneal injection of 4,5-dimethyl-3-(2-oxo-2-phenylethyl)-thiazolium chloride at a final concentration of 1 mM in the anterior chamber of one eye, and Barany's solution in the adjacent eye. Pretreatment measurements of intraocular pressure were determined after stimulating retro-orbital flow with injections of prostaglandin F2α (PGF2α) (2 µg). Needle outflow facility measurements were conducted under baseline and pilocarpine-stimulated (i.v.) condition at 3 weeks, 2 months, 3, 6, and 9 months post administration of 4,5-dimethyl-3-(2-oxo-2-phenylethyl)thiazolium chloride. The results are shown in Table 1 and FIGS. 1 and 2.

EXAMPLE 13

Penetration Study through an Intact Cornea in
Rabbits

Corneas were mounted in a chamber in vitro at 37° C. with the epithelial side exposed to 4,5-dimethyl-3-(2-oxo-2-phenylethyl)thiazolium chloride in Barany's Solution. 1 ml samples were taken from the endothelial side 1 hour after addition of 4,5-dimethyl-3-(2-oxo-2-phenylethyl)thiazolium chloride at a final concentration of 1 mM to the epithelial chamber. The volume of the chamber was replaced with phosphate buffered saline. The chromatogram shown above is from a 1 hour time point, with penetration calculated at 0.5%. The 1 ml sample was injected onto a 2 ml sample loop in an HPLC gradient system with a Medichem Inertsil ODS2, 5 micron column of dimensions 4.6×250 mm in 0.05 M sodium phosphate buffer, pH 7.4 with 10% acetonitrile. The gradient was from 10%-40% acetonitrile over 30 min. The chromatograms are shown in FIG. 3.

EXAMPLE 14

Penetration Study through an Intact Cornea in
Cynomologous Monkeys

An eye cup was set in place on one eye each of two monkeys and a 10 mM solution of 4,5-dimethyl-3-(2-oxo-2-phenylethyl)-thiazolium chloride in Barany's Solution was placed in the reservoir for a period of 5 hours. At the end of the experiment, the eye cup was removed, the eye was flooded repeatedly with Barany's Solution and a 10 µl sample of intraocular fluid was removed from the anterior chamber with a needle, inserted through the cornea. The 10 µl sample was injected using an automatic injector system an HPLC gradient system with a Medichem Inertsil ODS2, 5 micron column of dimensions 4.6×250 mm in 0.05 M sodium phosphate buffer, pH 7.4 with 10% acetonitrile.

EXAMPLE 15

Effect of
4,5-Dimethyl-3-(2-oxo-2-phenylethyl)thiazolium
chloride on Intramuscular Pilocarpine-Stimulated
Accommodative Response in Primates Animals were treated for 4 days, twice a day (once a day on weekends) with 2 µg PGF2α. On days 5-8 both eyes were treated first with 2 µg PGF2α followed 2 hours later with an intraocular injection of 10 µL of 4,5-dimethyl-3-(2-oxo-2-phenylethyl)thiazolium chloride at a final concentration of 1 MM in the eye. The needle was kept in the eye for 30 minutes post injection. No injection was made to the control eye. Twenty-four hours after the last injection of 4,5-dimethyl-3-(2-oxo-2-phenylethyl)thiazolium chloride, a course of therapy consisting of once a day dosing for a total of 4 days, accommodative responses to i.m. pilocarpine administration was performed following phenylephrine refraction. The results are depicted in FIG. 4.

EXAMPLE 16

Cross-Linking Inhibition Assay

The following method was used to evaluate the ability of the compounds to inhibit the cross-linking of glycated bovine serum albumin (AGE-BSA) to rat tail tendon collagen-coated 96-well plates.

AGE-BSA was prepared by incubating BSA at a concentration of 200 mg per ml with 200 mM glucose in 0.4M sodium phosphate buffer, pH 7.4 at 37° C. for 12 weeks. The glycated BSA was then extensively dialyzed against phosphate buffer solution (PBS) for 48 hours with additional 5 times buffer exchanges. The rat tail tendon collagen coated plate was blocked first with 300 microliters of Superbloc blocking buffer (Pierce Chemical, Rockford, Ill.) for one hour. The blocking solution was removed from the wells by washing the plate twice with phosphate buffered saline (PBS)-Tween 20 solution (0.05% Tween 20) using a NUNC-multiprobe (Nalge Nunc, Rochester, N.Y.) or Dynatech ELISA-plate (Dynatech, Alexandria, Va.) washer. Cross-linking of AGE-BSA (1 to 10 microgram per well depending on the batch of AGE-BSA) to rat tail tendon collagen coated plate was performed with and without the testing compound dissolved in PBS buffer at pH 7.4 at one or more desired concentrations by the addition of 50 microliters each of the AGE-BSA diluted in PBS or in the solution of test compound at 37° C. for 4 hours. Unbrowned BSA in PBS buffer with or without testing compound were added to the separate wells as the blanks. The un-cross-linked AGE-BSA was then removed by washing the wells three times with PBS-Tween buffer. The amount of AGE-BSA crosslinked to the tail tendon collagen-coated plate was then quantitated using a polyclonal antibody raised against AGE-RNase. After a one-hour incubation period, AGE antibody was removed by washing 4 times with PBS-Tween.

The bound AGE antibody was then detected with the addition of horseradish peroxidase-conjugated secondary antibody—goat anti-rabbit immunoglobulin and incubation for 30 minutes. The substrate of 2,2-azino-di(3-ethylbenzthiazoline sulfonic acid) (ABTS chromogen) (Zymed Laboratories, Inc., South San Francisco, Calif.) was added. The reaction was allowed for an additional 15 minutes and the absorbance was read at 410 nm in a Dynatech plate reader.

EXAMPLE 17

Cross-Link Breaking Assay

To ascertain the ability of the compounds of the instant invention to break or reverse already formed advanced glycosylation endproducts, a sandwich enzyme immunoassay was applied. Generally, the assay utilizes collagen-coated 96 well microtiter plates that are obtained commercially. AGE-modified protein (AGE-BSA) is incubated on the collagen-coated wells for four hours, is washed off the wells with PBS-Tween and solutions of the test compounds are added. Following an incubation period of 16 hours (37° C.) cross-link-breaking is detected using an antibody raised against AGE-ribonuclease or with an antibody against BSA.

Preparation of Solutions and Buffers

Bovine Serum Albumin (Type V) (BSA) (from Calbiochem) solution was prepared as follows: 400 mg of Type V BSA (bovine serum albumin) was added for each ml of 0.4 M sodium phosphate buffer, pH 7.4. A 400 mM glucose solution was prepared by dissolving 7.2 grams of dextrose in 100 ml of 0.4 M sodium phosphate buffer, pH 7.4. The BSA and glucose solutions were mixed 1:1 and incubated at 37° C. for 12 weeks. The pH of the incubation mixture was monitored weekly and adjusted to pH 7.4 if necessary. After 12 weeks, the AGE-BSA solution was dialyzed against PBS for 48 hours with four buffer changes, each at a 1:500 ratio of solution to dialysis buffer. Protein concentration was determined by the micro-Lowry method. The AGE-BSA stock solution was aliquoted and stored at −20° C.

Test compounds were dissolved in PBS and the pH was adjusted to pH 7.4, if necessary. AGE-BSA stock solution was diluted in PBS to measure maximum crosslinking and in the inhibitor solution for testing inhibitory activity of compounds. The concentration of AGE-BSA necessary to achieve the optimum sensitivity was determined by initial titration of each lot of AGE-BSA.

Substrates for detection of secondary antibody binding were prepared by diluting the HRP substrate buffer (Zymed) 1:10 in distilled water and mixing with ABTS chromogen (Zymed) 1:50 just prior to use.

Assay Procedures

Biocoat plates were blocked with 300 microliters of Superbloc (Pierce Chemical). Plates were blocked for one hour at room temperature and were washed with PBS-Tween (0.05% v/v) three times with the Dynatech platewasher before addition of test reagents.

The first three wells of the Biocoat plate were used for the reagent blank. Fifty microliters of solutions AGE-BSA were added to test wells in triplicate and only PBS in blank wells. The plate was incubated at 37° C. for four hours and washed with PBS-Tween three times. Fifty microliters of PBS was added to the control wells and 50 microliters of the test prospective agent was added to the test wells and blank. The plate was incubated overnight (approximately 16 hours) with prospective agent, followed by washing in PBS before addition of primary antibody.

(Prior to use, each lot of primary antibody, either anti-BSA or anti-RNase, was tested for optimum binding capacity in this assay by preparing serial dilutions (1:500 to 1:2000) and plating 50 microliters of each dilution in the wells of Biocoat plates. Optimum primary antibody was determined from saturation kinetics.) Fifty microliters of primary antibody of appropriate dilution, was added and incubated for one hour at room temperature. The plate was then washed with PBS-Tween.

Plates were incubated with the secondary antibody, FWP-(Goat-anti-rabbit), which was diluted 1:4000 in PBS and used as the final secondary antibody. The incubation was performed at room temperature for thirty minutes.

Detection of maximum crosslinking and breaking of AGE crosslinking was performed as follows. IP substrate (100 microliter) was added to each well of the plate and was incubated at 37° C. for fifteen minutes. Readings were taken in the Dynatech ELISA-plate reader.

Definition

Heterocycle. Except where heteroaryl is separately recited for the same substituent, the term "heterocycle" includes heteroaryl.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A method of decreasing intraocular pressure in an animal in need thereof, comprising administering to the animal
   an effective amount of pilocarpine; and
   an effective amount of a compound of the formula I:

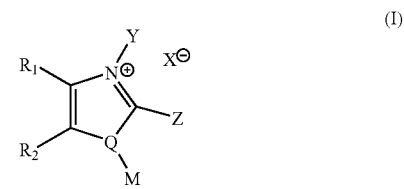

wherein
   $R^1$ and $R^2$ are independently selected from hydrogen, acylamino, acyloxyalkyl, alkanoyl, alkanoylalkyl, alkenyl, alkoxy, alkoxycarbonyl, alkoxycarbonylalkyl, alkyl, alkylamino, ($C_1$-$C_3$)alkylenedioxy, allyl, amino, ω-alkylenesulfonic acid, carbamoyl, carboxy, carboxyalkyl, cycloalkyl, dialkylamino, halo, hydroxy, ($C_2$-$C_6$) hydroxyalkyl, mercapto, nitro, sulfamoyl, sulfonic acid, alkylsulfonyl, alkylsulfinyl, alkylthio, trifluoromethyl, azetidin-1-yl, morpholin-4-yl, thiomorpholin-4-yl, piperidin-1-yl, 4-[$C_6$ or $C_{10}$]arylpiperidin-1-yl, 4-[$C_6$ or $C_{10}$]arylpiperazin-1-yl, or Ar, wherein Ar is $C_6$ or $C_{10}$ aryl or a 5- or 6-membered heteroaryl ring, wherein 6-membered heteroaryl ring contains one to three atoms of N, and the 5-membered heteroaryl ring contains from one to three atoms of N or one atom of O or S and zero to two atoms of N, each heteroaryl ring can be fused to a benzene, pyridine, pyrimidine, pyridazine, pyrazine, or (1,2,3)triazine, wherein the ring fusion is at a carbon-carbon double bond of Ar, Ar-alkyl, Ar—O, ArSO₂—, ArSO—, ArS—, ArSO₂NH—, ArNH, (N—Ar)(N- alkyl)N—, ArC(O)—, ArC(O)NH—, ArNH—C(O)—, or (N—Ar)(N-alkyl)N—C(O)—, or together $R^1$ and $R^2$ comprise methylenedioxy;

Z is hydrogen

Y is a group of the formula —CH($R^5$)—$R^6$ wherein $R^5$ is hydrogen;

$R^6$ is a group of the formula —W—$R^7$, wherein $R^7$ is Rs, wherein W is —C(=O)— and Rs is a $C_6$ aryl;

Q is S;

M is absent; and

X is a pharmaceutically acceptable anion, or a pharmaceutically acceptable salt of the compound, wherein aryl or Ar can be substituted with one or more substituents selected from the group consisting of acylamino, acyloxyalkyl, alkanoyl, alkanoylalkyl, alkenyl, alkoxy, alkoxycarbonyl, alkoxycarbonylalkyl, alkyl, alkylamino, ($C_1$-$C_3$)alkylenedioxy, alkylsulfonyl, alkylsulfinyl, ω-alkylenesulfonic acid, alkylthio, allyl, amino, ArC(O)—, ArC(O)NH—, ArO—, Ar—, Ar-alkyl-, carboxy, carboxyalkyl, cycloalkyl, dialkylamino, halo, trifluoromethyl, hydroxy, ($C_2$-$C_6$)hydroxyalkyl, mercapto, nitro, sulfamoyl, sulfonic acid, 1-pyrrolidinyl, 4-[$C_6$ or $C_{10}$]arylpiperazin-1-yl-, 4-[$C_6$ or $C_{10}$]arylpiperidin-1-yl, azetidin-1-yl, morpholin-4-yl, thiomorpholin-4-yl, and piperidin-1-yl, wherein the decreased intraocular pressure treats glaucoma.

2. The method of claim 1, wherein the compound of the formula I is 3-(2-phenyl-2-oxoethyl)-4,5-dimethylthiazolium chloride.

3. The method of claim 1, wherein said compounds are administered intravenously.

4. The method of claim 1, wherein said compounds are administered intracamerally.

5. The method of claim 1, wherein $R_1$ is alkyl.

6. The method of claim 1, wherein $R_2$ is alkyl.

7. The method of claim 1, wherein $R_1$ and $R_2$ are both alkyl.

8. The method of claim 1, wherein $R_1$ is methyl.

9. The method of claim 1, wherein $R_2$ is methyl.

10. The method of claim 1, wherein Rs is unsubstituted phenyl.

11. The method of claim 1, wherein X is halogen.

12. The method of claim 1, wherein X is chloride or bromide.

13. The method of claim 1, wherein the compound of formula I is 3-(2-phenyl-2-oxoethyl)-4,5-dimethylthiazolium bromide.

14. A method of decreasing intraocular pressure in an animal in need thereof, comprising administering to the animal an effective amount of pilocarpine and 3-(2-phenyl-2-oxoethyl)-4,5-dimethylthiazolium chloride wherein the decreased intraocular pressure treats glaucoma.

15. The method of claim 1, wherein the animal is a human.

16. The method of claim 14, wherein the animal is a human.

* * * * *